(12) United States Patent
Piehler et al.

(10) Patent No.: US 9,606,114 B2
(45) Date of Patent: Mar. 28, 2017

(54) MULTIVALENT CHELATORS CONTAINING A SCAFFOLD STRUCTURE FOR MODIFYING AND ORGANIZING OF TARGET MOLECULES

(75) Inventors: Jacob Piehler, Oberursel (DE); Robert Tampe, Oberursel (DE); Suman Lata, Oberursel (DE)

(73) Assignee: JOHANN WOLFGANG GOETHE-UNIVERSITAT FRANKFURT AM MAIN, Frankfurt am Main (DE)

( * ) Notice: Subject to any disclaimer, the term of this patent is extended or adjusted under 35 U.S.C. 154(b) by 1624 days.

(21) Appl. No.: 11/573,253

(22) PCT Filed: Jul. 26, 2005

(86) PCT No.: PCT/EP2005/008124
§ 371 (c)(1),
(2), (4) Date: Oct. 29, 2007

(87) PCT Pub. No.: WO2006/013042
PCT Pub. Date: Feb. 9, 2006

(65) Prior Publication Data
US 2008/0038750 A1    Feb. 14, 2008

Related U.S. Application Data

(60) Provisional application No. 60/614,950, filed on Sep. 29, 2004.

(30) Foreign Application Priority Data

Aug. 5, 2004 (DE) .................. 10 2004 038 134

(51) Int. Cl.
| | |
|---|---|
| C07D 257/02 | (2006.01) |
| G01N 33/543 | (2006.01) |
| A61K 49/00 | (2006.01) |
| B01D 15/38 | (2006.01) |
| B01J 20/32 | (2006.01) |
| B01J 45/00 | (2006.01) |
| B82Y 5/00 | (2011.01) |
| B82Y 10/00 | (2011.01) |
| B82Y 30/00 | (2011.01) |
| C07C 237/12 | (2006.01) |
| C07C 237/22 | (2006.01) |
| C07K 7/02 | (2006.01) |

(52) U.S. Cl.
CPC ... *G01N 33/54353* (2013.01); *A61K 49/0032* (2013.01); *A61K 49/0041* (2013.01); *A61K 49/0052* (2013.01); *B01D 15/3828* (2013.01); *B01J 20/3265* (2013.01); *B01J 45/00* (2013.01); *B82Y 5/00* (2013.01); *B82Y 10/00* (2013.01); *B82Y 30/00* (2013.01); *C07C 237/12* (2013.01); *C07C 237/22* (2013.01); *C07D 257/02* (2013.01); *C07K 7/02* (2013.01)

(58) Field of Classification Search
None
See application file for complete search history.

(56) References Cited

U.S. PATENT DOCUMENTS

| | | | |
|---|---|---|---|
| 4,835,269 | A | 5/1989 | Kahovec et al. |
| 6,123,923 | A | 9/2000 | Unger et al. |
| 6,241,968 | B1 | 6/2001 | Tournier et al. |
| 6,252,042 | B1 | 6/2001 | Tegge et al. |
| 2003/0068379 | A1 | 4/2003 | Li et al. |
| 2007/0258905 | A1 | 11/2007 | Aime et al. |

FOREIGN PATENT DOCUMENTS

| | | |
|---|---|---|
| CA | 2 304 458 | 8/1999 |
| DE | 3638482 | 5/1987 |
| JP | 1-139555 | 6/1989 |
| JP | 9-500660 | 1/1997 |
| JP | 2000-506125 | 5/2000 |
| JP | 2001-518471 | 10/2001 |
| JP | 2002-187948 | 7/2002 |
| JP | 2003-525306 | 8/2003 |
| JP | 2008-505141 | 2/2008 |
| WO | 95/31444 | 11/1995 |
| WO | 95/32004 | 11/1995 |
| WO | 97/32862 | 9/1997 |
| WO | WO 98/43082 | 10/1998 |
| WO | WO 00/32167 | 6/2000 |
| WO | WO 00/47548 | 8/2000 |
| WO | 01/64708 | 9/2001 |
| WO | 02/26724 | 4/2002 |
| WO | 0226721 | 4/2002 |
| WO | 03/011115 | 2/2003 |

OTHER PUBLICATIONS

Lata et al. Journal of the American Chemical Society, 2005, 127, 10205-10215.*
"Isomer", http://goldbook.iupac.org/I03289.html, accessed Dec. 16, 2013.*
Liu et al., "Convergent and Sequential Synthesis of Dendritic, Multivalent Complexing Agents" Synthesis, vol. 10, 2002, pp. 1398-1406.

(Continued)

*Primary Examiner* — Noble Jarrell
(74) *Attorney, Agent, or Firm* — McBee Moore Woodward & Vanik IP, LLC

(57) ABSTRACT

New compounds of the general formula $$X_m\text{-G-CL}_n$$

are described as well as methods for their production and use in the analysis, detection and purification of target molecules. These constitute multivalent chelator-compounds with an affinity-tag binding to metal-chelator-complexes which can selectively modify and/or immobilize target molecules by a multitude of probes or functional units.

8 Claims, 19 Drawing Sheets

(56) References Cited

OTHER PUBLICATIONS

Mier et al. "Synthesis of Peptide Conjugated Chelator Oligomers for Endoradiotherapy and MRT Imaging", Tetrahedron Letters, vol. 45 (2004) pp. 5453-5455.
Yang et al. "Facile N-1 Protection of Cyclam, Cyclen and 1,4,7-Triazacyclononane", Tetrahedron Letters, vol. 44 (2003) pp. 2481-2483.
Twyman et al. "The Synthesis of Chiral Dendritic Molecules Based on the Repeat Unit L-Glutamic Acid", Tetrahedron Letters, vol. 35 (1994) pp. 4423-4424.
European Office Action for 05768155.3, dated May 20, 2011.

* cited by examiner

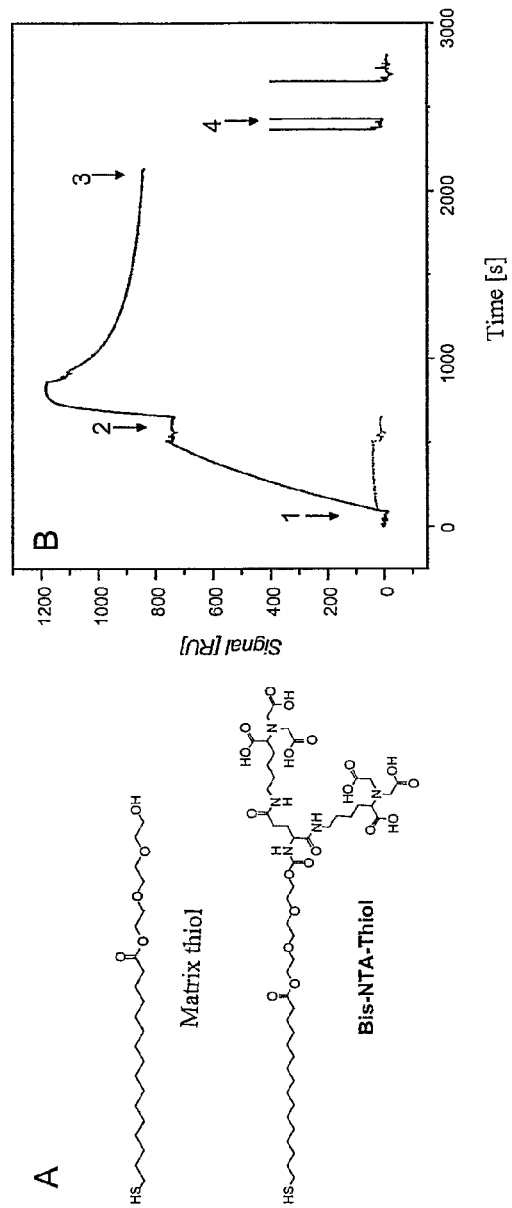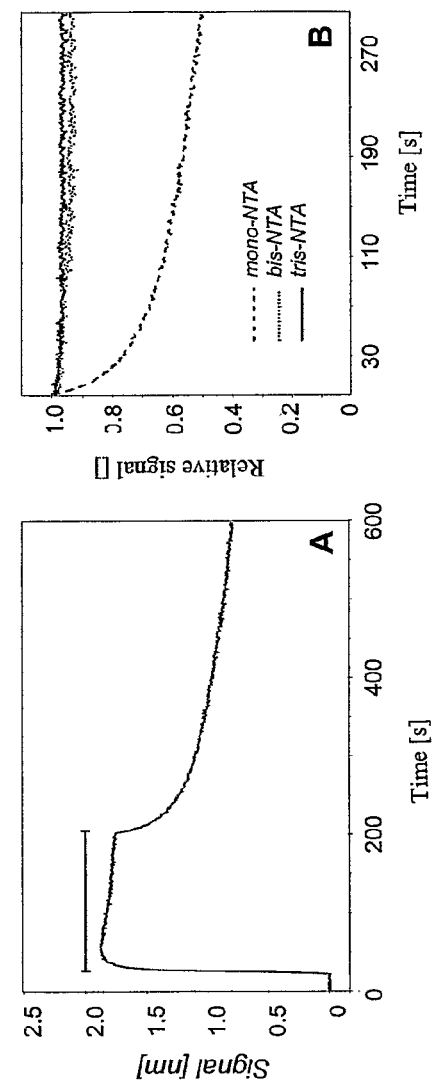
Figure 9
Figure 10

MULTIVALENT CHELATORS CONTAINING A SCAFFOLD STRUCTURE FOR MODIFYING AND ORGANIZING OF TARGET MOLECULES

CROSS-REFERENCE TO RELATED APPLICATIONS

This application is a National Stage entry of International Application No. PCT/EP2005/008124 filed 26 Jul. 2005, which claims priority to U.S. Provisional Application No. 60/614,950, filed 29 Sep. 2004, and to German Application No. DE 10 2004 038 134.8, filed Aug. 5, 2004; the contents of all of which are incorporated by reference in their entireties.

DESCRIPTION OF THE INVENTION

The present invention relates to multivalent chelator-compounds, methods for their production and their use for the modification and/or immobilization of target molecules that carry an affinity-tag binding to metal-chelator-complexes.

BACKGROUND OF THE INVENTION

The selective, non-covalent modification of recombinant proteins with spectroscopic or microscopic probes or (bio) chemically functional units is a central challenge for proteome-analysis and biotechnological uses. In principle, such modifications can be realized with local specificity by means of so-called affinity-tags, i.e. short peptide sequences that are introduced into a protein by genetic engineering. These affinity-tags are specifically recognized by (bio)chemical recognition units. While for purification several affinity-tags were used very successfully, their use for the attachment of spectroscopic or microscopic probes and other biochemical functional units in solution and to surfaces is often critical, since the complexes exhibit an insufficient stability.

Since the middle of the seventies, the chelator iminodiacetic acid (IDA) has already been used in combination with several metal ions for purifying of proteins (Porath J, Carlsson J, Olsson I, Belfrage G. 1975. Metal chelate affinity chromatography, a new approach to protein fractionation. *Nature* 258(5536):598-9.).

In the middle of the eighties, nitrilotriacetic acid (NTA) was described as a chelator for purifying of proteins (EP 0 253 303 B1, U.S. Pat. No. 4,877,830). Furthermore, the (cumulated) histidine-tag was described for the generic purification of recombinant proteins (Hochuli E, Dobel H, Schacher A. 1987. New metal chelate adsorbent selective for proteins and peptides containing neighboring histidine residues. *J Chromatogr* 411:177-84; see EP 0 282 042 B1, U.S. Pat. No. 5,284,933). Today, the histidine-tag with is by far the most commonly used affinity-tag, and most diverse matrices and detection techniques that rely on the interaction of oligohistidin with chelator-bound metal ions are described (Ueda E K, Gout P W, Morganti L. 2003. Current and prospective applications of metal ion-protein binding. *J Chromatogr A* 988(1):1-23.). Nevertheless, the binding affinity of individual Ni-NTA-oligohistidine-interactions is too low in order to ensure a stable and stoichiometrically defined binding. A partially stable binding can be achieved through a high density of NTA-groups in an affinity matrix or a planar surface (see e.g. Dorn I. T., Pawlitschko K., Pettinger S. C., Tampe R. 1998. Orientation and two-dimensional organization of proteins at chelator lipid interfaces. *Biol Chem.* 379(8-9):1151-9.; Frenzel A, Bergemann C, Kohl G, Reinard T. 2003. Novel purification system for 6xHis-tagged proteins by magnetic affinity separation. *J Chromatogr B Analyt Technol Biomed Life Sci.* 793(2):325-9.; Paborsky L R, Dunn K E, Gibbs C S, Dougherty J P. 1996. A nickel chelate microtiter plate assay for six histidine-containing proteins. *Anal Biochem.* 234(1):60-5.; Lauer S A, Nolan J P. 2002. Development and characterization of Ni-NTA-bearing microspheres. *Cytometry.* 48(3): 136-45.) For many uses, in particular for the manipulation of proteins in solution or in vivo, such as in living cells, nevertheless, a high binding stability at a molecular level is required.

First, in order to improve the binding between affinity-tag and metal-chelator, it is one possibility to manipulate the affinity-tag. Thus, on the one hand, extended histidine-tags are described, such as by Guiget et al., which use 10 histidine-residues instead of the common 6 (Guignet E G, Hovius R, Vogel H. 2004. Reversible site-selective labeling of membrane proteins in live cells. *Nat Biotechnol.* 22(4): 440-4.). Nevertheless, in this manner neither stoichiometrically defined nor stable complexes can be achieved. On the other hand, proteins and protein complexes are described that carry two histidine-tags and therefore bind more stably to the surfaces of Ni-NTA-chips (Nieba L, Nieba-Axmann S E, Persson A, Hamalainen M, Edebratt F, Hansson A, Lidholm J, Magnusson K, Karlsson A F, Plückthun A. 1997. BIACORE analysis of histidine-tagged proteins using a chelating NTA sensor chip. *Anal Biochem.* 252(2):217-28.). Nevertheless, not all proteins can be provided with more than one affinity-tag at their termini without too much affecting their biological functions.

The other possibility in order to increase the binding consists of improving the chelator group itself. Thus, Ebright and Ebright in WO 03/091689 (and in Kapanidis A N, Ebright Y W, Ebright R H. 2001. Site-specific incorporation of fluorescent probes into protein: hexahistidine-tag-mediated fluorescent labeling with (Ni(2+):nitrilotriacetic Acid (n)-fluorochrome conjugates. *J Am Chem Soc.* 123(48): 12123-5.) describe bivalent chelator complexes for in situ labelling of proteins with a detectable group, such as, for example, a fluorophor. These complexes show an improved affinity for His-tags, compared to the monovalent complexes. The two chelator-groups (NTA), nevertheless, are directly bound at the detectable group, making them not universally accessible for synthesis. Rather, the possibility for their production will always depend from the synthetic compatibility of the selected detectable group.

Other bifunctional carboxymethyl-substituted chelators are described by Kline et al. (Kline S J, Betebenner D A, Johnson D K. 1991. Carboxymethyl-substituted bifunctional chelators: preparation of aryl isothiocyanate derivatives of 3-(carboxymethyl)-3-azapentanedioic acid, 3,12-to(carboxymethyl)-6,9-dioxa-3,12-diazatetradecanedioic acid, and 1,4,7,10-tetraazacyclododecane-N,N',N'',N'''-tetraacetic acid for use as protein labels. *Bioconjug Chem.* 2(1):26-31.). These chelators can covalenty bind the target protein, and were developed for a labelling with metal-complexes with catalytic activity.

Another strategy for a stable and selective labelling or modification of target proteins is described by Griffin et al. (Griffin B A, Adams S R, Tsien R Y. 1998. Specific covalent labeling of recombinant protein molecules inside live cells. *Science.* 281(5374):269-72.). Bi-arsenic-complexes are disclosed that specifically recognize a particular motif in recombinant proteins containing four cysteines (Cys-Cys-Xaa-Xaa-Cys-Cys). The bi-arsenic-complexes can contain detectable groups such as fluorophores, and thus modify or label the target proteins. This technology is also described by Tsien et al. in U.S. Pat. No. 6,008,378, and by Ebright and Ebright in WO 03/107010. The use of these bi-arsenic-complexes, nevertheless, is limited by the laborious synthesis of the respective bi-arsenic-derivatives as well as by the fact that only particular fluorophores and chromophores are possible. In addition, the cysteine-rich affinity-tags or motifs as required are disadvantageous for many uses due to the high reactivity of free thiol groups.

It is therefore the object of the present invention to provide multivalent chelators for binding to affinity-tags that are known and widely used in the state of the art, such as the oligo-histidine-tag, that exhibit a stoichiometric, stable interaction with the affinity-tag and interact switchable and reversible with the target molecule. By this, target molecules can be generically modified with a multitude of probes and other biochemically functional units in a selective and position-specific manner. Furthermore, the multivalent chelators shall be synthetically accessible in such a way that a controlled and universal conjugation with a multitude of probes and other biochemically functional units is possible.

According to the invention, this object is solved by providing of compounds of the general formula $X_m$-G-$CL_n$ wherein G is a scaffold-structure, X is a coupling group for a probe or functional unit F, CL is a chelator-group with at least a metal-coordinative centre, m is an integer and at least 1, and n is an integer and at least 2, and tautomers, isomers, anhydrides, acids and salts thereof.

In a preferred embodiment, the scaffold-structures G comprise a saturated hydrocarbon chain with 2 to 25 carbon-atoms, preferred 2 to 20 and further preferred 5 to 16 carbon-atoms. Furthermore, the scaffold-structures comprise amide-, ester- and/or ether bonds.

The scaffold-structure can be linear, branched or closed. A preferred closed scaffold-structure is represented by a cyclam ring structure. Preferred scaffold-structures comprise amino acid-elements.

In a preferred embodiment, at least one metal ion is bound to each of the chelator-groups of the compounds according to the invention. Thereby, the metal ion is selected from the group consisting of $Ni^{2+}$, $Co^{2+}$, $Cu^{2+}$, $Zn^{2+}$, $Fe^{2+}$, $Fe^{3+}$, and all lanthanidions.

The chelator-group is preferably selected from the group consisting of nitrilotriacetic acid (NTA), iminodiacetic acid (IDA), all variants of porphyrine systems, salicylic acid derivatives, 1,2-diaminoethyldiacetic acid, diaminoethyl triacetic acid, hydroxy ethylimino diacetic acid, and salts or combinations thereof, and other chelator-groups known to the person of skill.

In a preferred embodiment, the reactive groups of the chelator-group carry protective groups. For example, carboxyl-groups such as those of NTA can be protected by the OtBu-group. All common protective groups known to the person of skill can be used.

In a further embodiment a spacer group A is located between the chelator-groups and the scaffold-structure. The spacer group A can be linear or branched. The usual spacer groups that are known to the person of skill can be used.

Preferred spacer groups comprise poly(ethylene glycol), oligo(ethylene glycol), peptides, $(CH_2)_n$, wherein n is from 1 to 8, oligoproline.

It is preferred that the chelator-groups are bound to the scaffold-structure through amide, ester or ether bonds.

According to the invention, it is preferred that the scaffold-structure G itself is not a probe or another detectable group. Preferably, G is a structure at which the chelator-groups and probes or functional units are attached.

Preferably, the compounds according to the invention are selected from

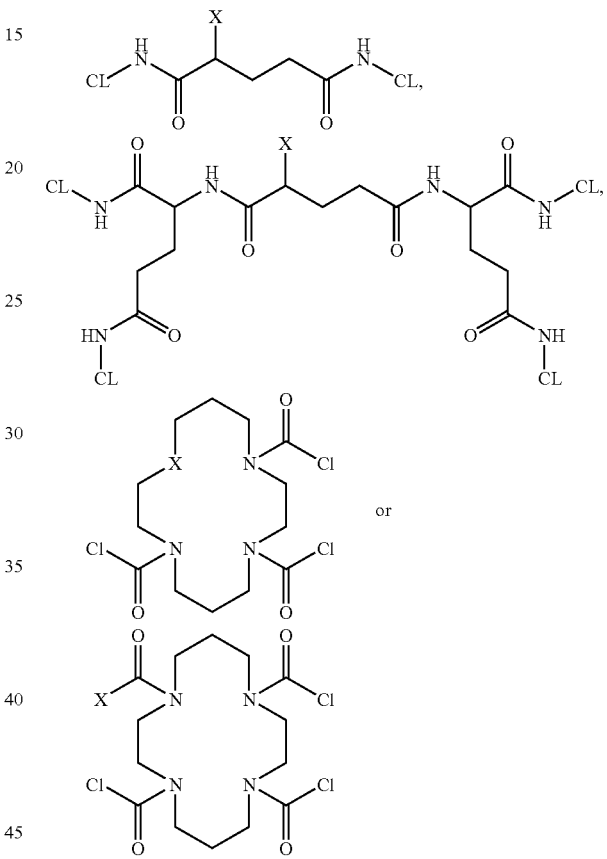

and from the tautomers, isomers, anhydrides, acids and salts thereof.

Preferred coupling groups X are selected from the group consisting of NHR, wherein R is H, an alkyl or aryl residue, COOH, $(CH_2)_n$—COOH, wherein n is an integer, SH, maleinimide, iodoacetamide, isothiocyanate or cyanate.

In a preferred embodiment, a probe or functional unit F is bound at the coupling group X of the compound according to the invention. The probe or functional unit F is preferably selected from the group consisting of fluorophores, FRET-fluorophores, fluorescence quenchers, phosphorescent compounds, luminescent compounds, absorbing compounds, polymers, PEG, oligosaccharides, oligonucleotides, PNA, biotin, haptenes, peptides, proteins, enzymes, cross linking agents, oligo(ethylene glycol), lipids, nanoparticles, electron density amplifiers, gold clusters, metal clusters, quantum dots, and combinations thereof.

Examples for fluorophores and chromophores that are suitable as probes can be found in Haughland R. P. 1996.

Handbook of Fluorescent Probes and Research Chemicals, Molecular Probes, 6th Ed. (Spence, MTZ, ed.).
Preferably the compounds according to the invention are selected from
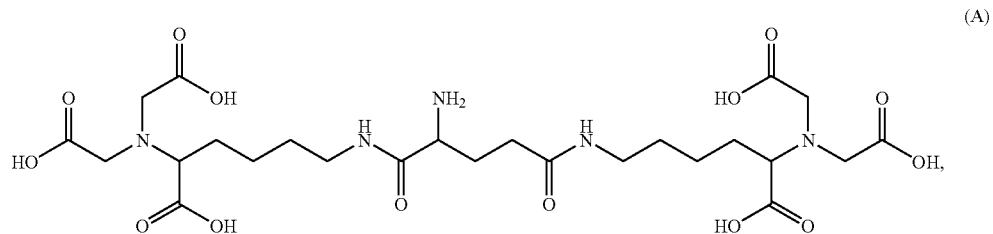
(A)
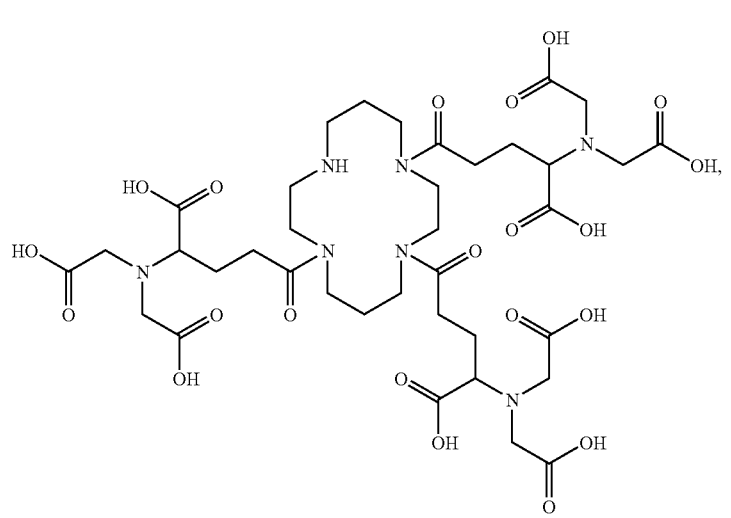
(B)
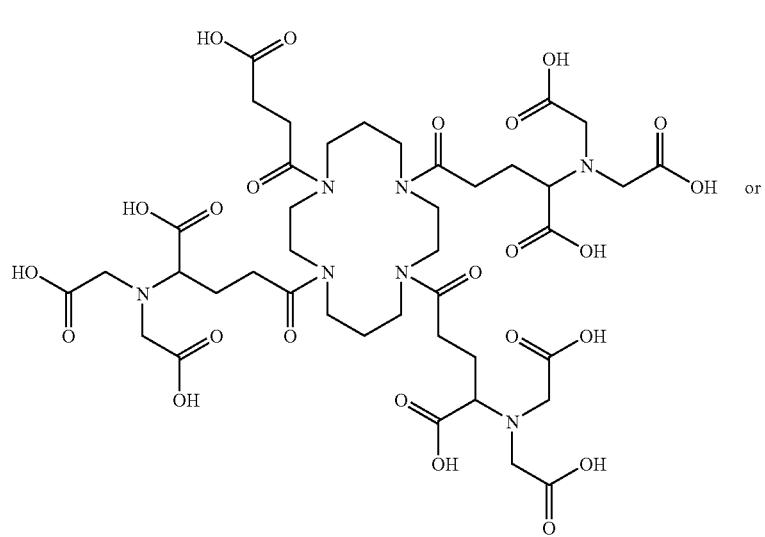
(C) or

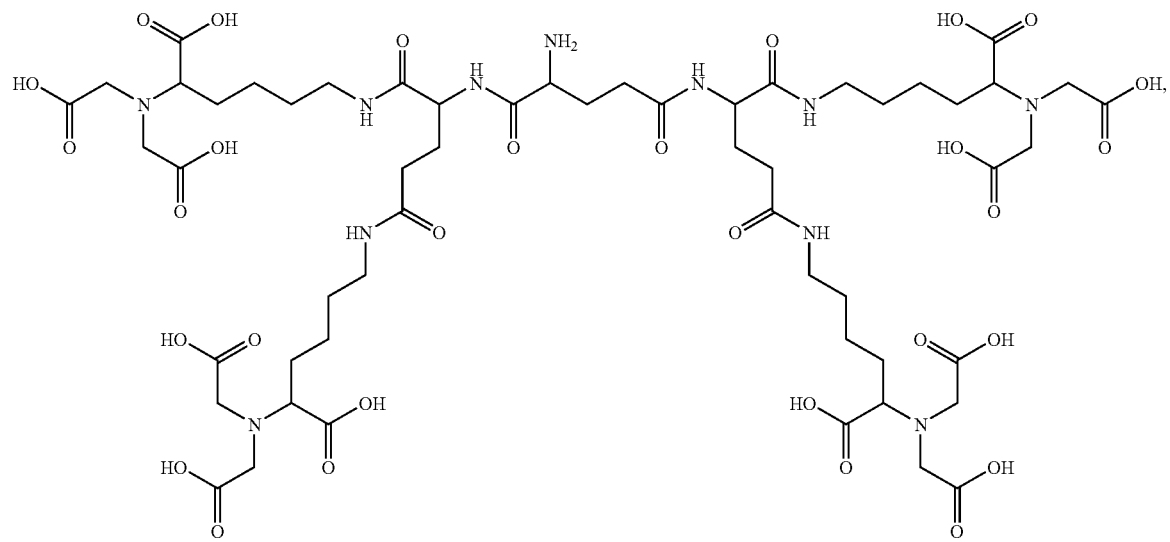

(D)

wherein (A) is bis-NTA, (B) and (C) is tris-NTA and (D) is tetrakis-NTA (see also FIG. 1), and tautomers, isomers, anhydrides, acids and salts thereof.

In general, said multivalent chelators can be characterized in that several (independent) chelator-groups, nevertheless preferably 2 to 4, such as nitrilotriacetic acid (NTA), can be attached to a molecular scaffold (scaffold G), whereas at the same time a functional group (coupling group X) is provided for coupling to a probe or functional unit F. An important prerequisite for the attachment to probes or functional units is the chemical orthogonality of this coupling group X to the functional groups of the chelator-groups, such as three carboxyl groups in case of NTA. In case of the multivalent chelators as shown in FIG. 1 this was achieved by protective groups at the carboxyl groups (cf. FIG. 2). Now, selective coupling reactions at the additional functional group (X) can be performed without that the chelator-groups are affected.

Furthermore, the object is solved by providing a method for producing the compounds according to the invention. The method comprises the coupling of at least two chelator-groups to the scaffold-structure subsequent or during the synthesis of the scaffold-structure, wherein the chelator-groups can be protected in a suitable manner. During the method according to the invention, the coupling group X can also be suitably protected.

The synthesis of the scaffold-structure according to the invention comprises the synthesis from one or several starting compounds, in particular from amino acids, such as lysine, ornithine, 1,3-diaminobutyric acid, 1,2-diaminopropionic acid, glutamate or aspartate and/or their protected derivatives, such as Z-Lys-OtBu, H-Glu(OtBu)-OBzl, Z-Glu-OH.

Further preferred starting compounds are bromoacetic acid-tert-butylester, BOC-☐-aminocaproic acid as well as macrocyclic polyamines, such as 1,4,8,11-tetraazacyclotetradecane.

A preferred intermediate is N□,N□-bis[(tert-butyloxycarbonyl)methyl]-L-lysine-tert-butylester ("Lys-NTA-OtBu", compound 3 in FIG. 25).

The method for production according to the invention preferably first comprises a synthesis of the scaffold-structure. Then, the chelator-groups are coupled to said scaffold-structure. Thereby, the chelator-groups can carry suitable protective groups. Thereby, the scaffold-structure preferably is a cyclic scaffold-structure, such as a cyclam ring structure.

The method for production according to the invention comprises that the scaffold-structure can be composed from protected amino acids or from compounds derived from amino acids. For this, it is preferred that already during the synthesis of the scaffold-structure protected chelator-groups are included. The starting compounds for the scaffold-structure can constitute typical starting products of peptide synthesis that are known to the person of skill. For this, the preferred scaffold-structure is linear or branched (i.e. dendrimeric).

It is preferred that carboxyl-functionalized scaffold-structures with amino-functionalized, protected chelator-groups or amino-functionalized scaffold-structures with carboxyl-functionalized, protected chelator-groups are modified.

In scheme I, a schematic representation of preferred synthesis pathways can be found. In (A), a carboxyl-based scaffold with an amino-functionalized, protected chelator-element (see also FIG. 3A) is modified. The protected functional group (coupling group) X—P is deprotected either selectively (I), or together with the chelator-groups (II), and subsequently can be coupled with a probe or functional unit F. (B) shows an analogous synthesis pathway for an amino-functionalized scaffold that is modified with a carboxyl-functionalized, protected chelator-element (see also FIG. 3B). The intermediates 1 or 2, in turn, can be used as chelator-elements in the first step of the synthesis (see also example 9).

Scheme I

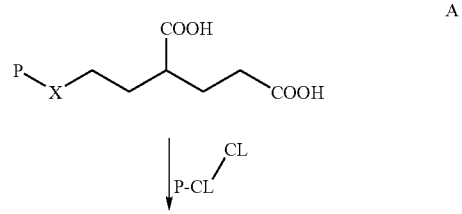

A

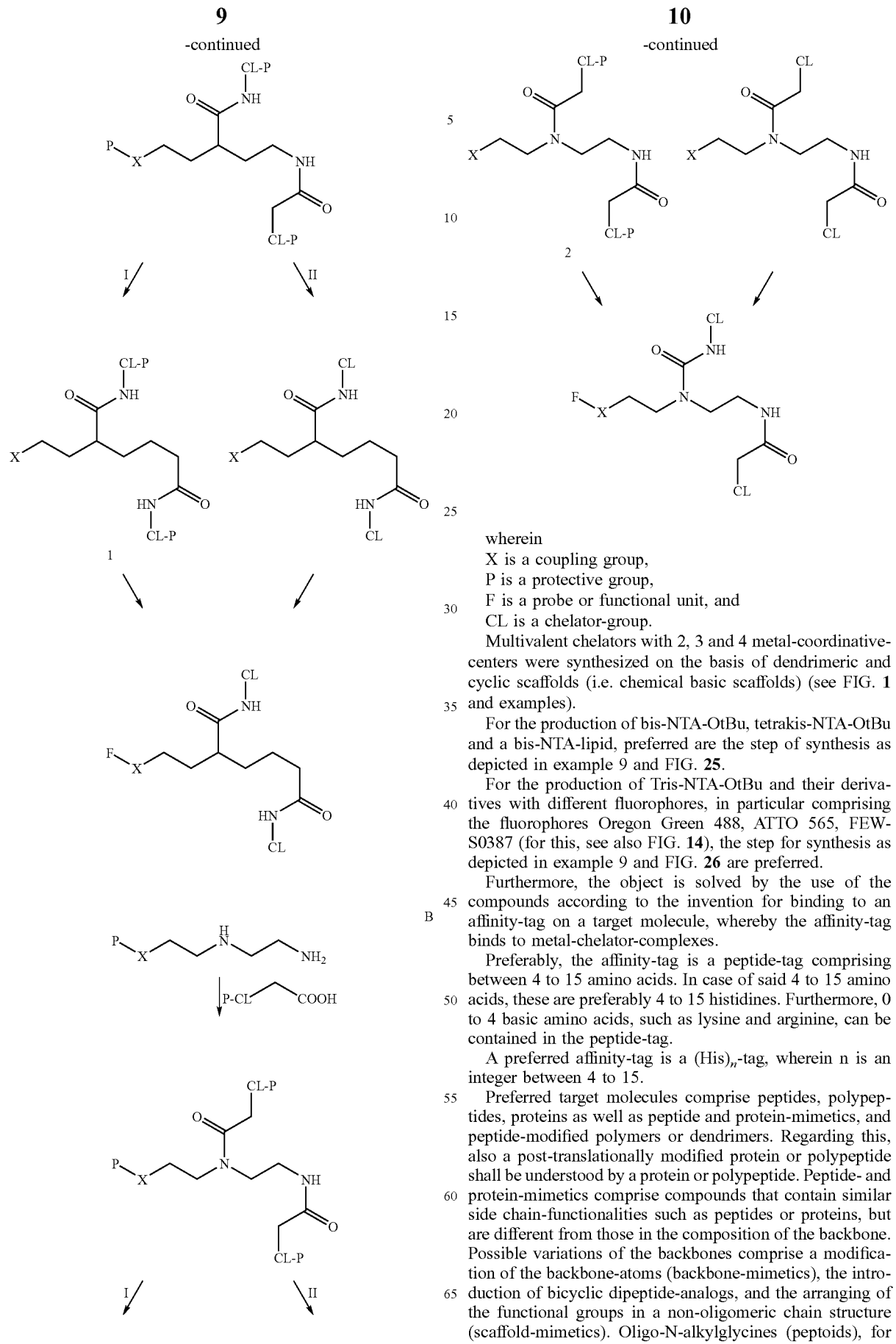

wherein
X is a coupling group,
P is a protective group,
F is a probe or functional unit, and
CL is a chelator-group.

Multivalent chelators with 2, 3 and 4 metal-coordinative-centers were synthesized on the basis of dendrimeric and cyclic scaffolds (i.e. chemical basic scaffolds) (see FIG. 1 and examples).

For the production of bis-NTA-OtBu, tetrakis-NTA-OtBu and a bis-NTA-lipid, preferred are the step of synthesis as depicted in example 9 and FIG. 25.

For the production of Tris-NTA-OtBu and their derivatives with different fluorophores, in particular comprising the fluorophores Oregon Green 488, ATTO 565, FEW-S0387 (for this, see also FIG. 14), the step for synthesis as depicted in example 9 and FIG. 26 are preferred.

Furthermore, the object is solved by the use of the compounds according to the invention for binding to an affinity-tag on a target molecule, whereby the affinity-tag binds to metal-chelator-complexes.

Preferably, the affinity-tag is a peptide-tag comprising between 4 to 15 amino acids. In case of said 4 to 15 amino acids, these are preferably 4 to 15 histidines. Furthermore, 0 to 4 basic amino acids, such as lysine and arginine, can be contained in the peptide-tag.

A preferred affinity-tag is a $(His)_n$-tag, wherein n is an integer between 4 to 15.

Preferred target molecules comprise peptides, polypeptides, proteins as well as peptide and protein-mimetics, and peptide-modified polymers or dendrimers. Regarding this, also a post-translationally modified protein or polypeptide shall be understood by a protein or polypeptide. Peptide- and protein-mimetics comprise compounds that contain similar side chain-functionalities such as peptides or proteins, but are different from those in the composition of the backbone. Possible variations of the backbones comprise a modification of the backbone-atoms (backbone-mimetics), the introduction of bicyclic dipeptide-analogs, and the arranging of the functional groups in a non-oligomeric chain structure (scaffold-mimetics). Oligo-N-alkylglycines (peptoids), for example, belong to the backbone-mimetics, which differ from peptides or proteins in the point of attachment of the side chain (at the N instead of the $C_\alpha$).

Preferably, the compounds according to the invention can be used for the modification, immobilization, coupling, purification, detection, monitoring, analysis, or for a detection of target molecules in vitro, in vivo, in situ, in fixed and living cells or in lipid vesicles.

A further preferred use of the compounds according to the invention is the controlled and reversible dimerization or oligomerization of target molecules, in particular proteins, to supra-molecular functional units.

The compounds according to the invention can be used in numerous in vitro and in vivo assay methods that are known in the state of the art. Preferred assay methods comprise spectroscopic methods such as absorption spectroscopy, fluorescence spectroscopy, fluorescence-resonance-energy transfer (FRET), fluorescence-correlation-spectroscopy (FCS), fluorescence-bleaching (fluorescence recovery after photobleaching, FRAP), reflectometric interference-spectroscopy (RIfS), surface-plasmon-resonance-spectroscopy (surface plasmon resonance)/BIACORE, optical scanning coupling, quartz-micro balance, surface acoustic waves (SAW), x/y-fluorescence-scanning (FluorImaging) as well as microscopic methods such as fluorescence-microscopy, confocal optical microscopy, total internal reflection-microscopy, contrast enhancing microscopy, electron microscopy, scanning probe microscopy, but also other methods such as magnet resonance spectroscopy, microscopy and tomography, impedance-spectroscopy, field-effect-transistors, enzyme-linked immunoabsorbent assay (ELISA), fluorescence-activated cell or particle-sorting (FACS), radioimmunoassay (RIA), autoradiography, analytical gel filtration, stopped-flow technique, calorimetry, high throughput screening, (HTS), array- and chip-technologies, such as protein-arrays.

Further preferred is the use of the compounds according to the invention for the immobilization of target molecules.

For this, the compounds of the invention can be bound onto a surface or included in a lipid-mono or double layer. Thereby, the surface is preferably selected from glass type-surfaces, such as metalloid oxides, metal oxides and all glass types/glasses, gold, silver, DAPEG-modified glass, PEG-polymer-modified glass or gold, GOPTS-silanized glass, glass type or noble metal surfaces with lipid-mono or double layer, metal selenides, tellurides and sulfides.

By a glass-surface a glass type-surface shall be understood that in addition to glass also comprises quartz, mica, metal oxides, metalloid oxides.

The use of the according to the invention for the production of self-assembled mono layers (SAM) on noble metal surfaces is preferred. SAM are preferably used in methods that are based on surface-plasmon-resonance-spectroscopy, impedance-spectroscopy, scanning probe microscopy, and quartz-micro balance.

Furthermore, the compounds of this invention can be used for the production of functional micro and/or nano-structured surfaces and of protein-arrays.

It is a basic idea of the present invention to use the redundancy of the oligo histidine-tag in order to increase the stability of the protein-chelator-binding by several magnitudes through multivalent chelators (MCH).

The binding of oligo histidine-tags to metal-chelator-complexes in general occurs by a coordinative binding of the N-atoms of the imidazole-residues of the oligo histidine-tags to free coordinative positions in the $Ni^{2+}$ that is complexed by the chelator, and thus partially coordinatively saturated.

In case of Ni-NTA-complexes, four of the overall six coordinative positions of the $Ni^{2+}$ are saturated by NTA, such that two free coordinative positions for the binding of 2 histidine-residues remain (FIG. 4A). The complex formation thus requires two steps (FIG. 4B): (1) the activation of the chelator by binding of a metal ion, such as e.g. $Ni^{2+}$, and (2) the binding of histidine-residues of the oligo histidine-tag to the free coordinative positions. By addition of free imidazole in excess the binding of the oligo histidine-tag to the Ni(II)-chelator-complex can be abolished, such that the protein-chelator binding is reversible and switchable. In addition, the chelator can be deactivated by a removal of the $Ni^{2+}$ from the chelate-complex using EDTA (FIG. 4B).

The binding of the oligo histidine-tag to metal chelate-complexes through only two histidine-residues is relatively unstable (see examples 4 and 8). If metal chelators are immobilized in high density, then several histidine-residues of the oligo histidine-tag can simultaneously bind to several metal-chelate-units resulting to a stronger binding (FIG. 5B). Through the use of multivalent chelators that contain several metal-chelate-units in one molecule, a stable binding to oligo histidine-tags on the molecular level can be achieved. By coupling of further functional units to the chelator, proteins that contain an oligo histidine-tag can be modified stably, but reversibly and switchable (FIG. 5C).

The examinations as described in the following Figures and examples show that the multivalent chelator-compounds represent chemical, highly-affine, switchable molecular recognition structures for affinity-tags, such as the histidine-tag. Thus, they do not only represent an improvement of the traditional chelators, but principally open novel areas of use. Since they can be coupled with nearly any chemical compound, with these chelators nearly any kind of spectroscopic or microscopic probe or functional unit can be attached location-specifically and reversibly an target molecules, such as recombinant proteins. Also, e.g. oligosaccharides, PEG or other biochemical functional units can be reversibly bound to target molecules in order to in this way functionally modify these. In turn, MCH can also be put onto molecular scaffolds and by this way sterically organize target molecules, such as e.g. proteins, in dimeric or multimeric structures. Again, here the versatile switchability is a central feature. Further possibilities result from a coupling with oligonucleotides or PNA. Thus, the multiplexing-possibilities of the DNA-microarrays could be used for the production of protein-arrays.

The following abbreviations are used:
AU absorbance units
Boc tert-butyloxycarbonyl (protective group)
Bzl benzyl (protective group)
DAPEG α,ω-diaminopoly(ethylene glycol)
DIC diisopropylcarbodiimide
DMF dimethylformamide
DIPEA diisopropylethylamine
EDTA ethylenediamine tetraacetic acid
FL fluorescein
FRET fluorescence resonance energy transfer
Glu glutamic acid
GOPTS glycidyloxipropyltriethoxysilane
H10 deca-histidine
H6 hexa-histidine
IDA iminodiacetic acid
Ifnar2 extracellular domain des type I interferon-receptor 2
IFNα2, IFNβ type I interferons α2 and β
MBP maltose binding protein
MCH multivalent Chelator NTA nitrilotriacetic acid
OG Oregon Green 488®
PEG poly(ethylene glycol)
PNA peptide nucleic acid
RIFS reflectometric interference-spectroscopy
RT room temperature
SAM self-assembling mono layer
TBTU O-(beizotriazole-1-yl)-N,N,N',N'-tetramethylurollium tetrafluoroborate
tBu tertiary-butyl (protective group)
TEA triethylamine
TFA trifluoro acetic acid
Z benzyloxycarbonyl (protective group)

FIGURES AND EXAMPLES

The present invention shall be further clarified by the following examples with reference to the attached Figures, nevertheless, without being limited to these examples.

In the Figures

(A) Mono-NTA (1) bis-NTA (2) and tris-NTA (3) with OtBu-protected NTA-groups. The free functional group (coupling group X) is hatched in grey.

(B) the same chelators as in (A) after coupling of the functional group to a PEG-probe and de-protection of the carboxyl groups of the NTA-residues.

Figure 3:
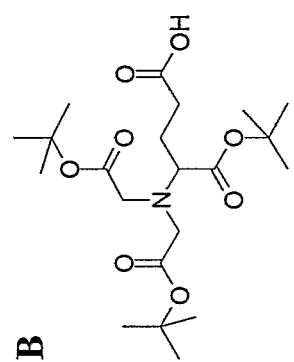
Figure 3:
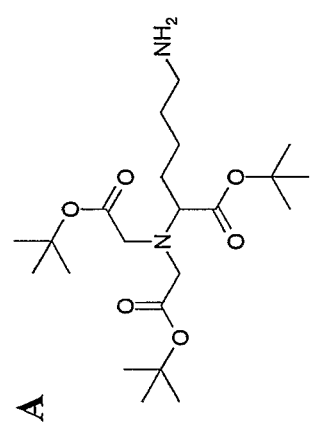

FIG. 3 shows preferred, protected amino-(A) or carboxyl-functionalized (B) chelator-elements (X—CL-P), such as in particular used in Scheme I.

Figure 4:
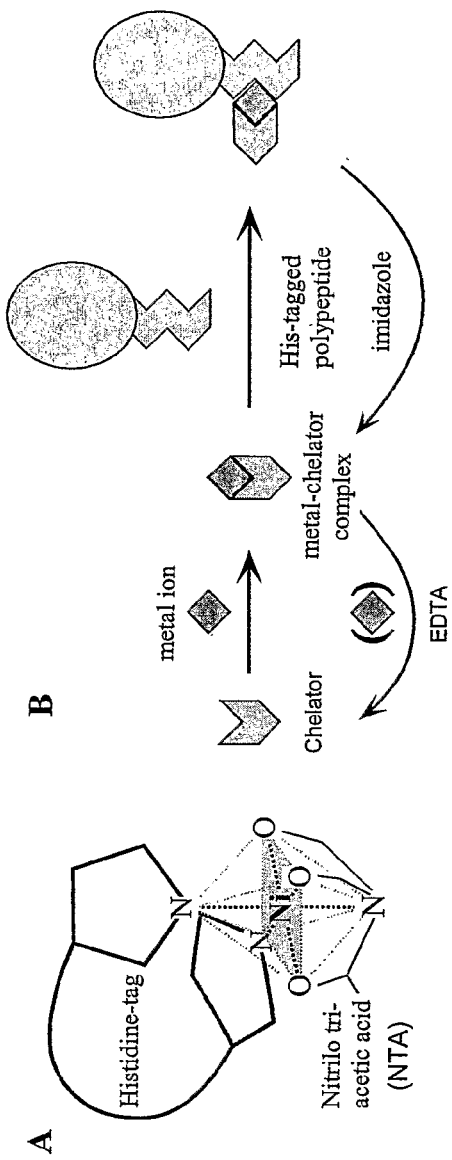

FIG. 4: shows the principle of the switchable, reversible interaction of oligo-histidine with metal-chelator-complexes.

(A) Coordination of two histidine residues to the two free coordinative positions of the Ni(II)-NTA-complex.

Figure 5:
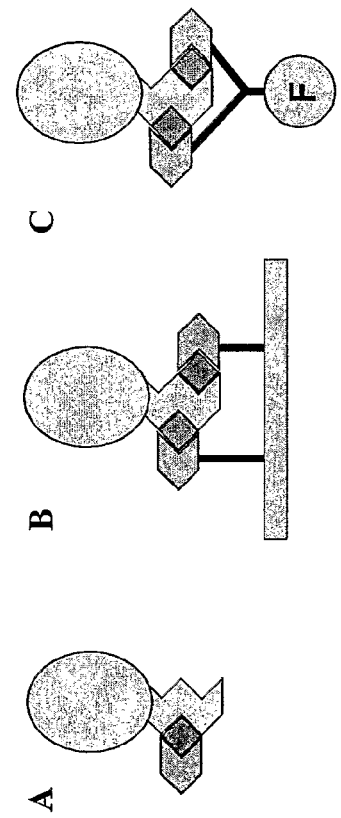

(B) Activation of chelators by means of metal ions and binding to histidine-tagged protein; dissociation by means of competitor (e.g. imidazole), and deactivation of the chelator e.g. using EDTA FIG. 5: shows the concept of the multivalent chelators.

(A) transient, monovalent interaction of immobilized metal chelators such as e.g. Ni:NTA with a histidine-tagged protein.

(B) Stable, multivalent interaction with 2 or more immobilized metal chelators, such as e.g. in an affinity matrix.

(C) stable coupling to functional units by multivalent chelators.

Figure 6:
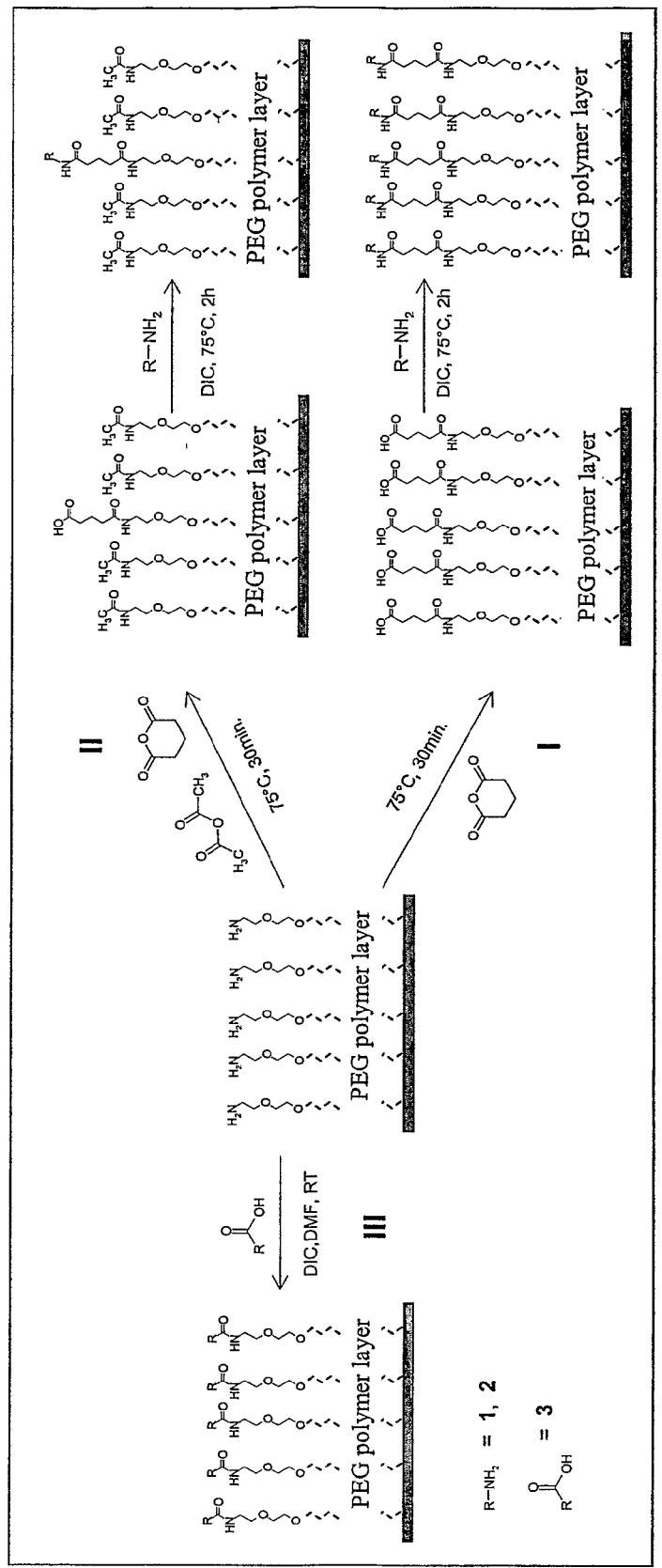

FIG. 6 shows a schematic illustration of the coupling of MCH to DAPEG-modified surfaces (see example 1).

Figure 7:
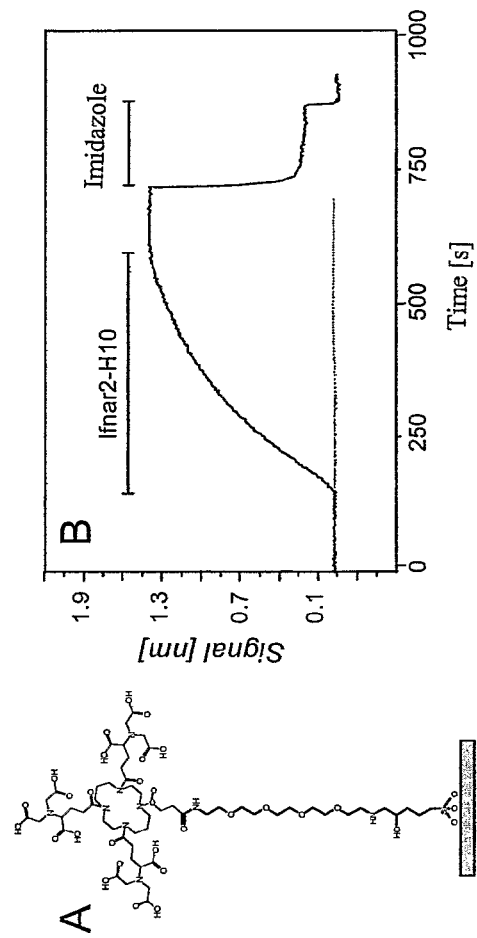

FIG. 7 shows protein-immobilization to functionalized glass surfaces.

(A) schematic illustration of the attachment of tris-NTA via a PEG-polymer layer (PEG2000) to a GOPTS-silanized glass surface.

(B) binding of ifnar2-H10 before ( . . . ) and after (-) loading of the chelator with Ni(II)-ions.

Figure 8:
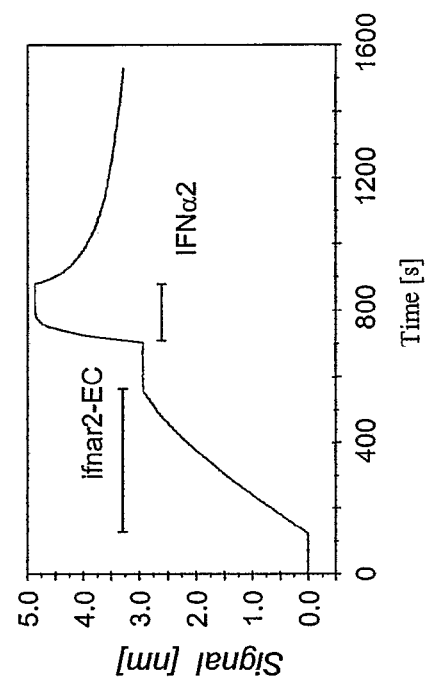

FIG. 8 shows the functionality of immobilized proteins on chelator-modified quartz surfaces (detected by RIFS). Binding curve for the immobilization of ifnar2-H10 after loading of the chelator with Ni(II)-ions and the interaction of immobilized ifnar2-H10 with its ligand IFN☐2.

FIG. 9 shows the immobilization of histidine-tagged proteins onto gold surfaces.

(A) structural formulae of alkylthiols that were used for the production of mixed self-assembled mono layers (SAM).

(B) binding of ifnar2-H6 (1) before ( . . . ) and after (-) loading of the surface-bound chelator with Ni(II)-ions, interaction with IFN☐2 (2) and regeneration with 200 mM imidazole (3) and 200 mM EDTA (4) (detection by means of surface plasmon-resonance).

FIG. 10 shows the comparison of the interaction of MBP-H10 in high concentration (30 μM) with different chelators.

(A) association and dissociation of 30 μM MBP-H10 to mono-NTA.

(B) dissociation in comparison for mono-, bis- and tris-NTA. (-).

Figure 11:
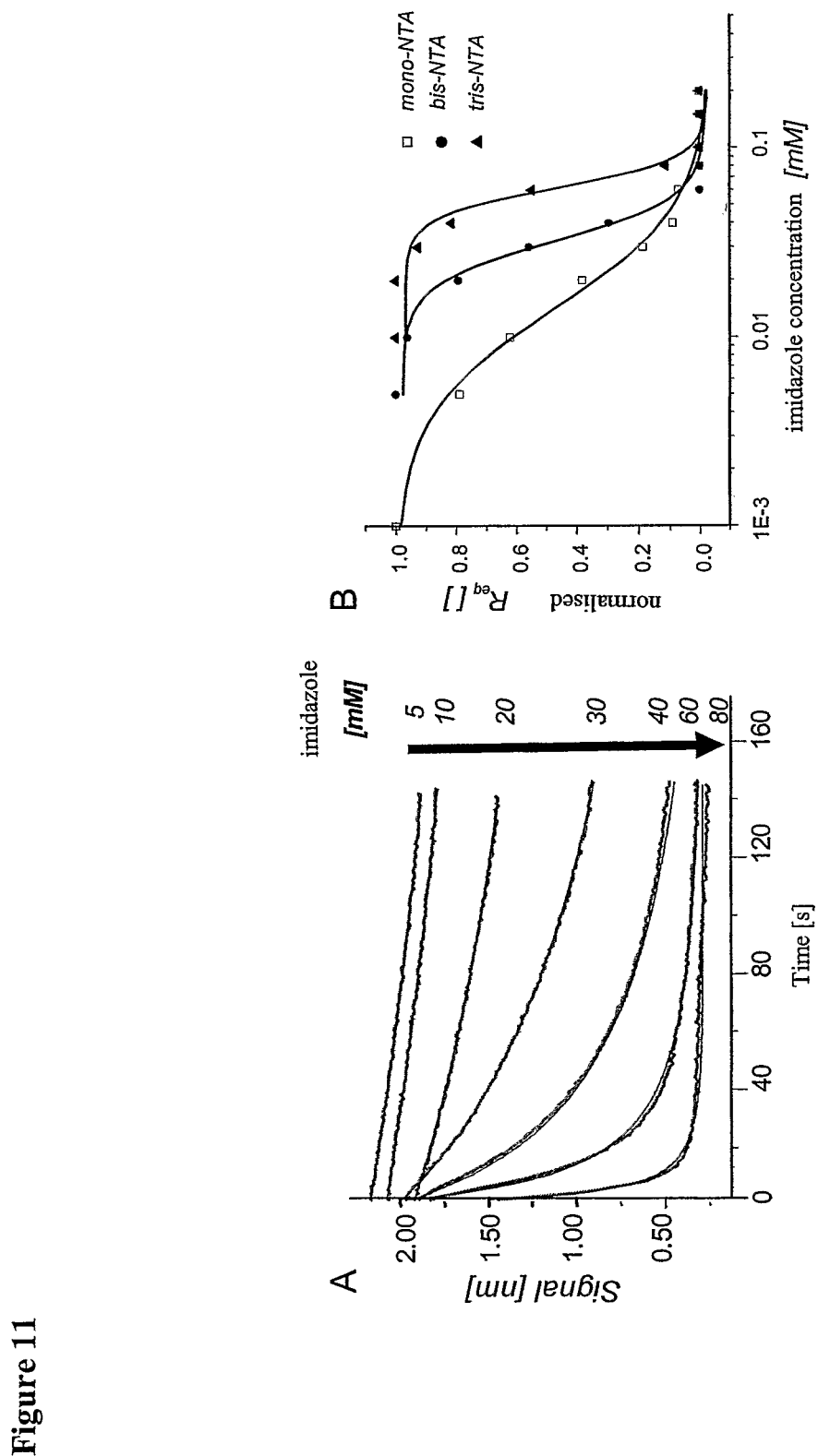

FIG. 11 shows the induced dissociation of immobilized MBP-H10 at different concentrations of imidazole.

(A) comparison of the dissociation kinetics of ifnar2-H10 of mono-NTA surfaces at different concentrations of imidazole and fitting of a binding model.

(B) dependency of the equilibrium-loading as a function of concentration of imidazole, compared for mono-, bis-, and tris-NTA.

FIG. 12

(A) shows the comparison of the stability of the binding of MBP-H6 and MBP-H10 to tris-NTA.

(B) comparison of the stability of the binding of MBP-H10 to mono-NTA, and of MBP-H6 to tris-NTA.

Figure 13:
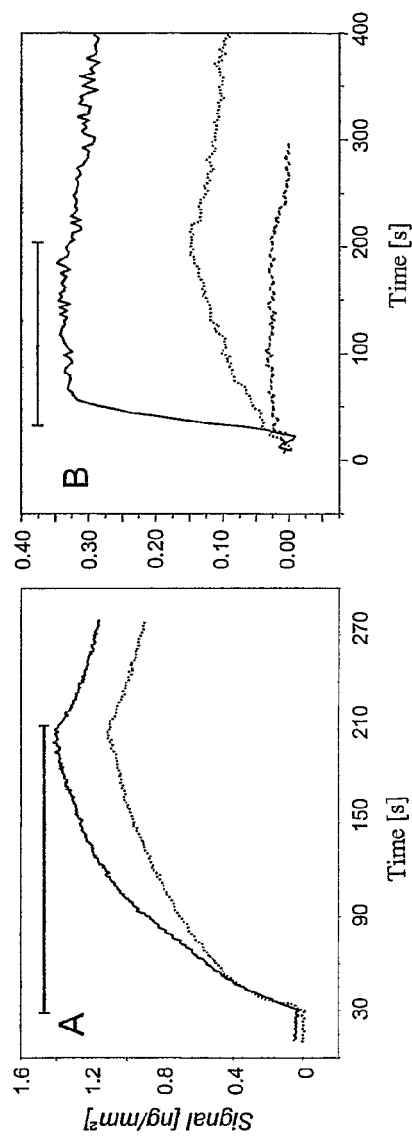

FIG. 13 shows the unspecific binding of proteins to chelator-modified surfaces.

(A) binding of IFNβ before ( . . . ) and after (-) immobilization of ifnar2-H10 to mono-NTA with high surface density.

(B) binding of IFNβ to tris-NTA with low surface density ( . . . ), after blocking of the surface with MBP-H10 (-), and after immobilization of ifnar2-H10 and subsequent blocking with MBP-H10 (-).

Figure 14:
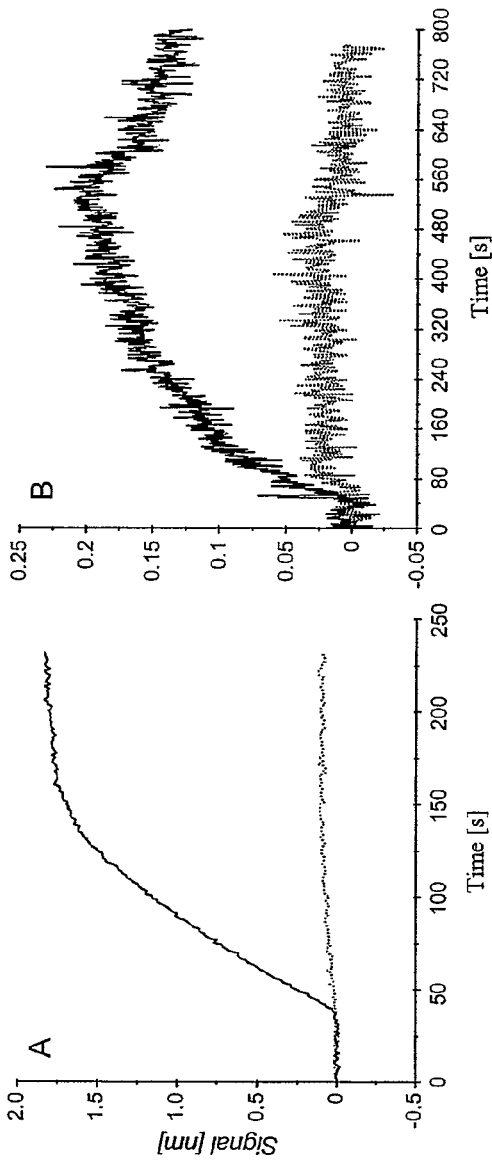

FIG. 14 shows the blocking of histidine-tags in solution by means of tris-NTA.

(A) binding of 50 nM ifnar1-H10 without (-) and with ( . . . ) 100 nM tris-NTA onto tris-NTA modified surfaces.

(B) binding of 100 nM ifnar1-H10 wt (-) and 100 nM ifnar1-H10 W129A ( . . . ) with each 200 nM tris-NTA-fluorescein to immobilized IFNβ.

Figure 15:
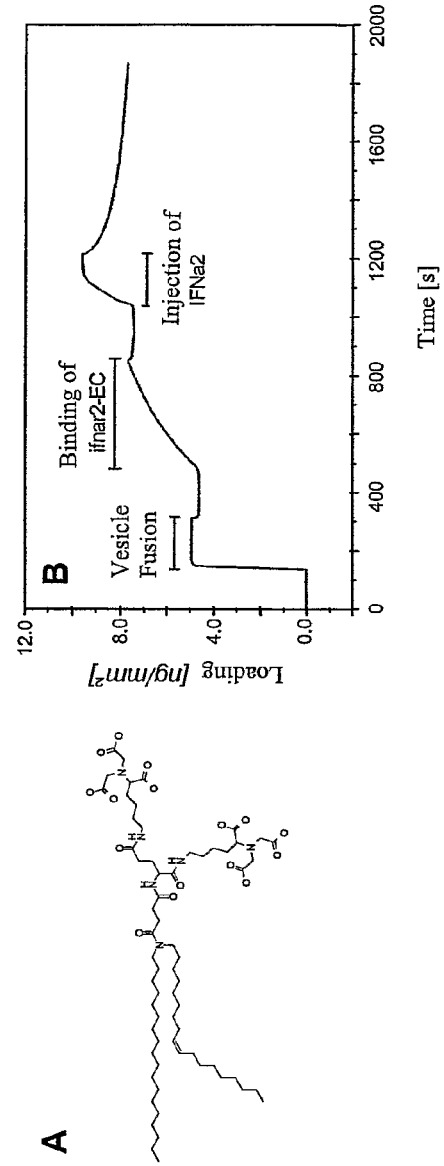

FIG. 15 shows the chelator-lipid conjugate for the attachment of histidine-tagged proteins to lipid membranes.

(A) structure of the synthesized bis-NTA lipid conjugate.

(B) assembly of solid-supported lipid double layers by vesicle fusion, immobilization of ifnar2-H10 and interaction with the ligand IFNα2.

Figure 16:
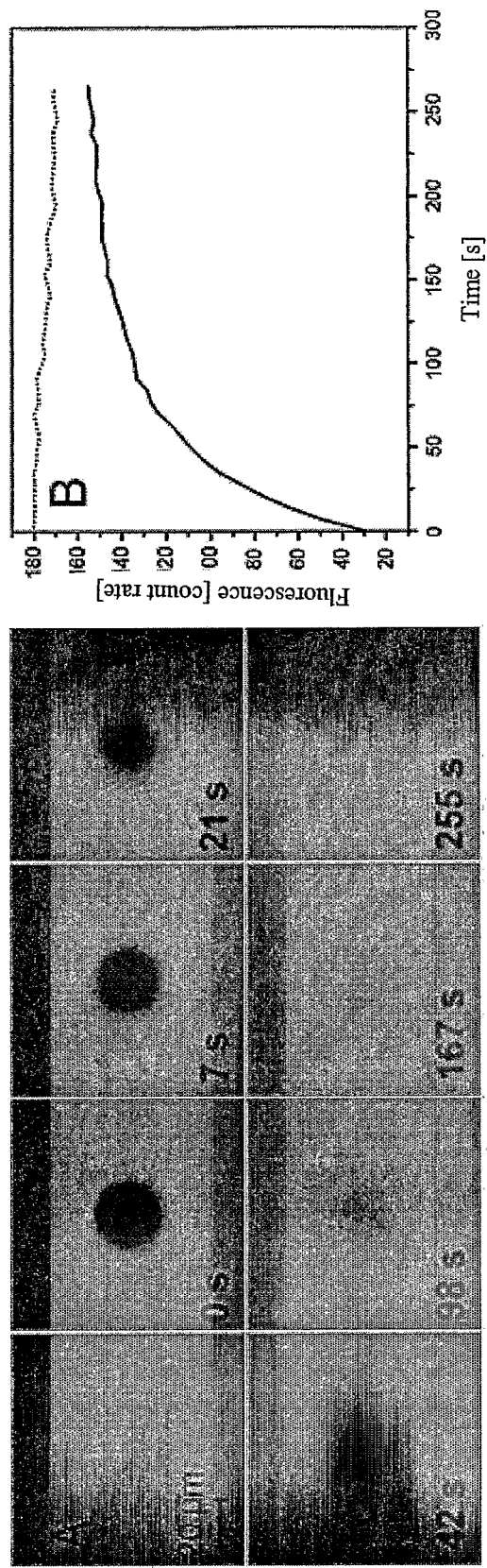

FIG. 16 shows the examination of the lateral diffusion of fluorescence-labeled ifnar2-H10, which was bound via FRAP to solid-supported lipid double layers. (A) Fluorescence-images before and at different points in time after the leaching of a circular section.

(B) intensity in the bleaching spot (-) and at a reference spot ( . . . ) as function of time.

Figure 17:
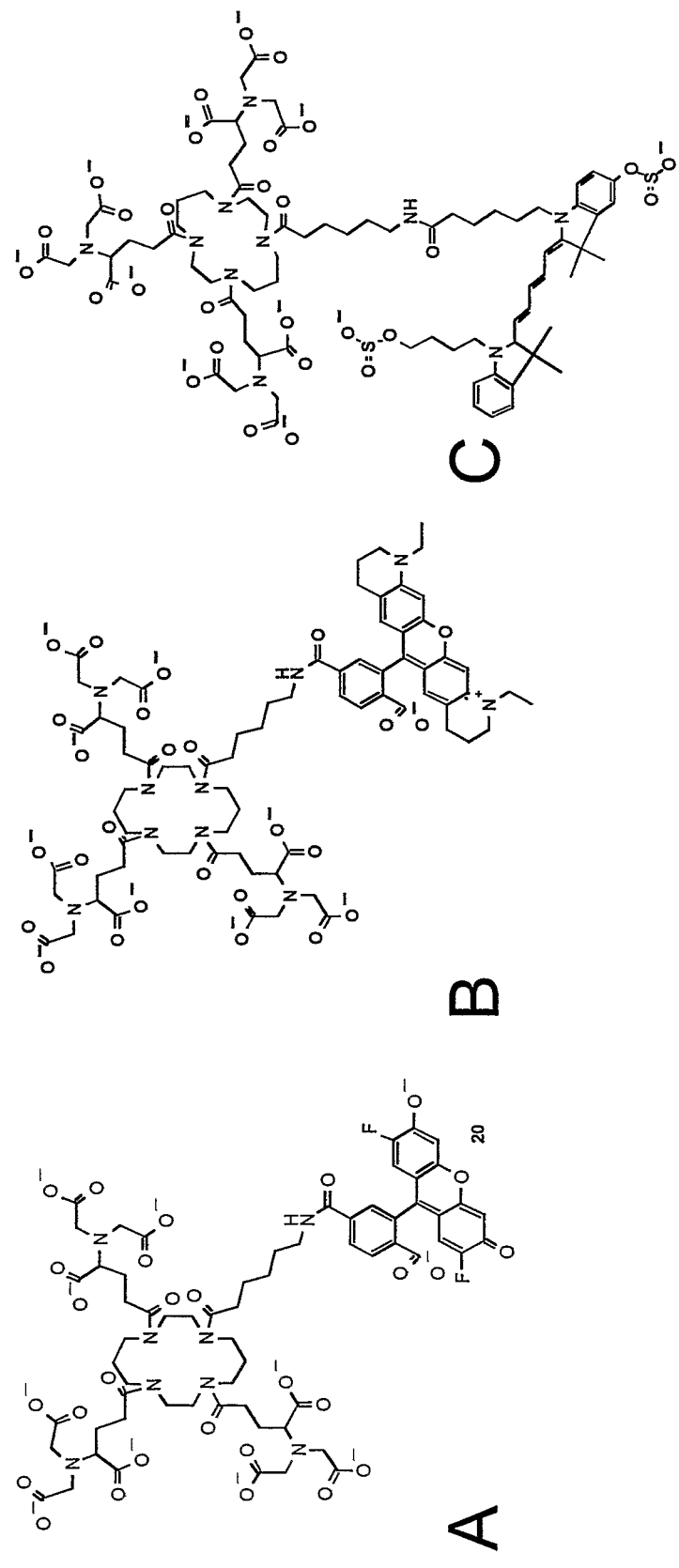

FIG. 17 shows conjugates of tris-NTA with different fluorophores

A: Oregon Green 488; B: ATTO 565; C: FEW-S0387.

Figure 18:
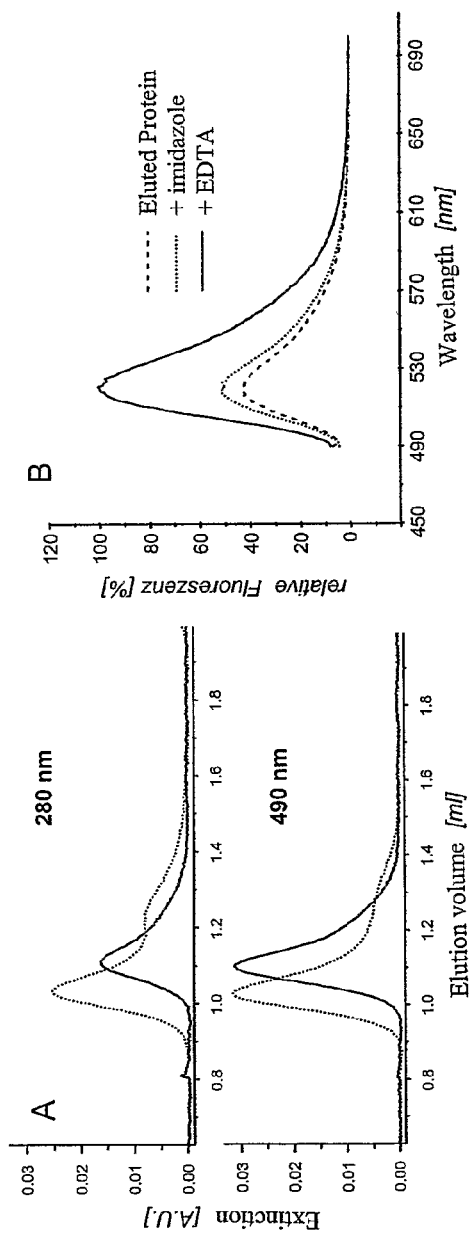

FIG. 18 shows fluorescent labeling and binding assay by means of gel filtration. (A) chromatogram (absorption at 280 (protein) or 490 nm (Oregon Green)) of ifnar2-H10 labeled with tris-NTA-Oregon Green before (-) and after ( . . . ) addition of the ligand IFNα2.

(B) fluorescence spectra of the tris-NTA-Oregon Green before (-) and after ( . . . ) loading with metal ions, and after binding to ifnar2-H10 (-).

Figure 19:
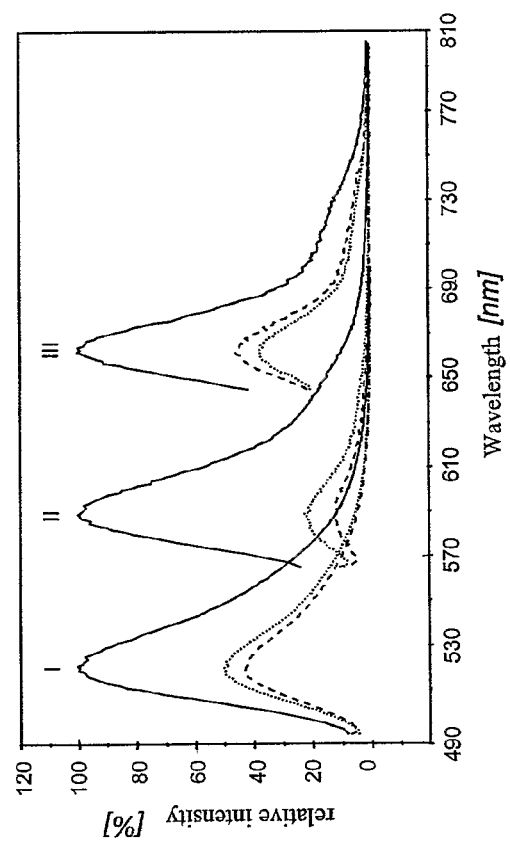

FIG. 19 shows the spectroscopic properties of the conjugates of tris-NTA with Oregon Green 488 (I), ATTO565 (II) and FEW-S0387 (III). Normalized fluorescence spectra of the conjugates (-), after complexing of Ni(II)-ions ( . . . ), and after binding of ifnar2-H10 (-).

Figure 20:
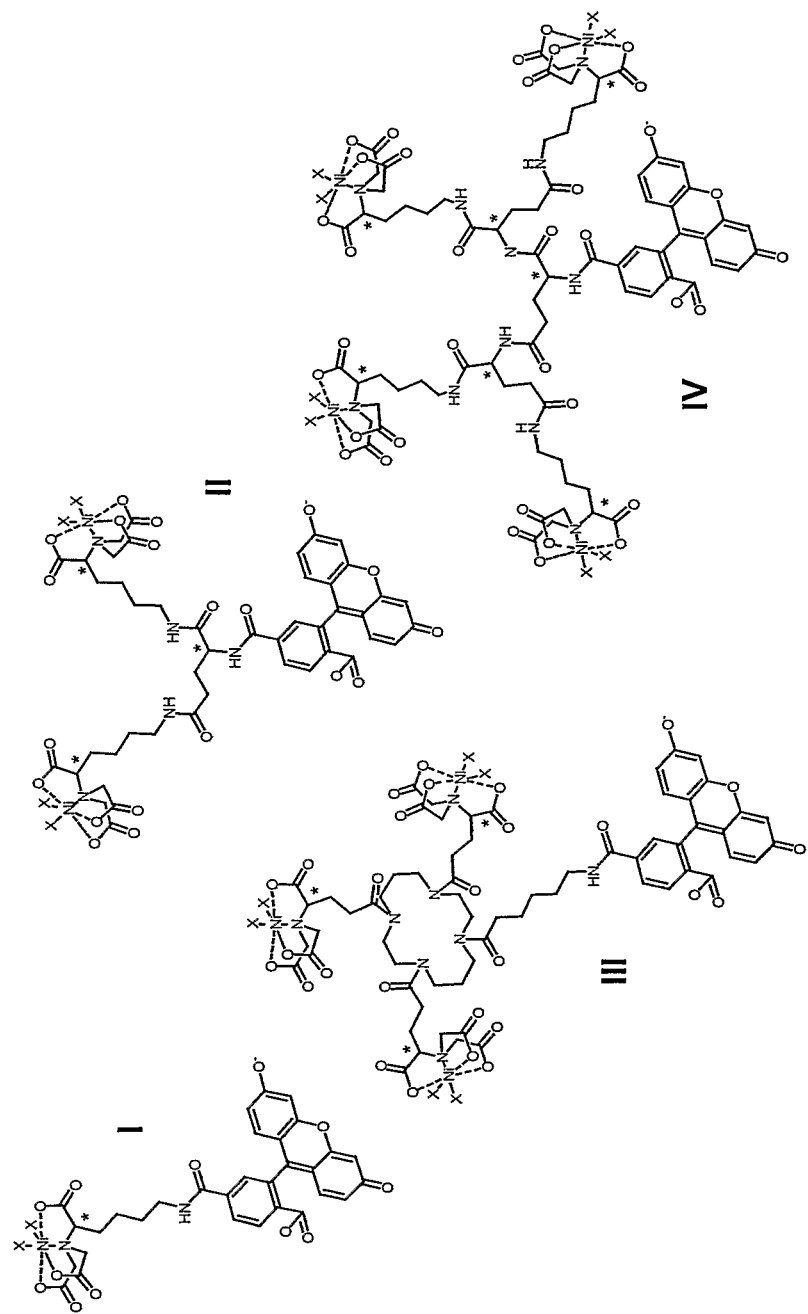

FIG. 20 shows the conjugates of mono-(A), bis-(B), tris-(C), and tetrakis-NTA (D) with fluorescein.

Figure 21:
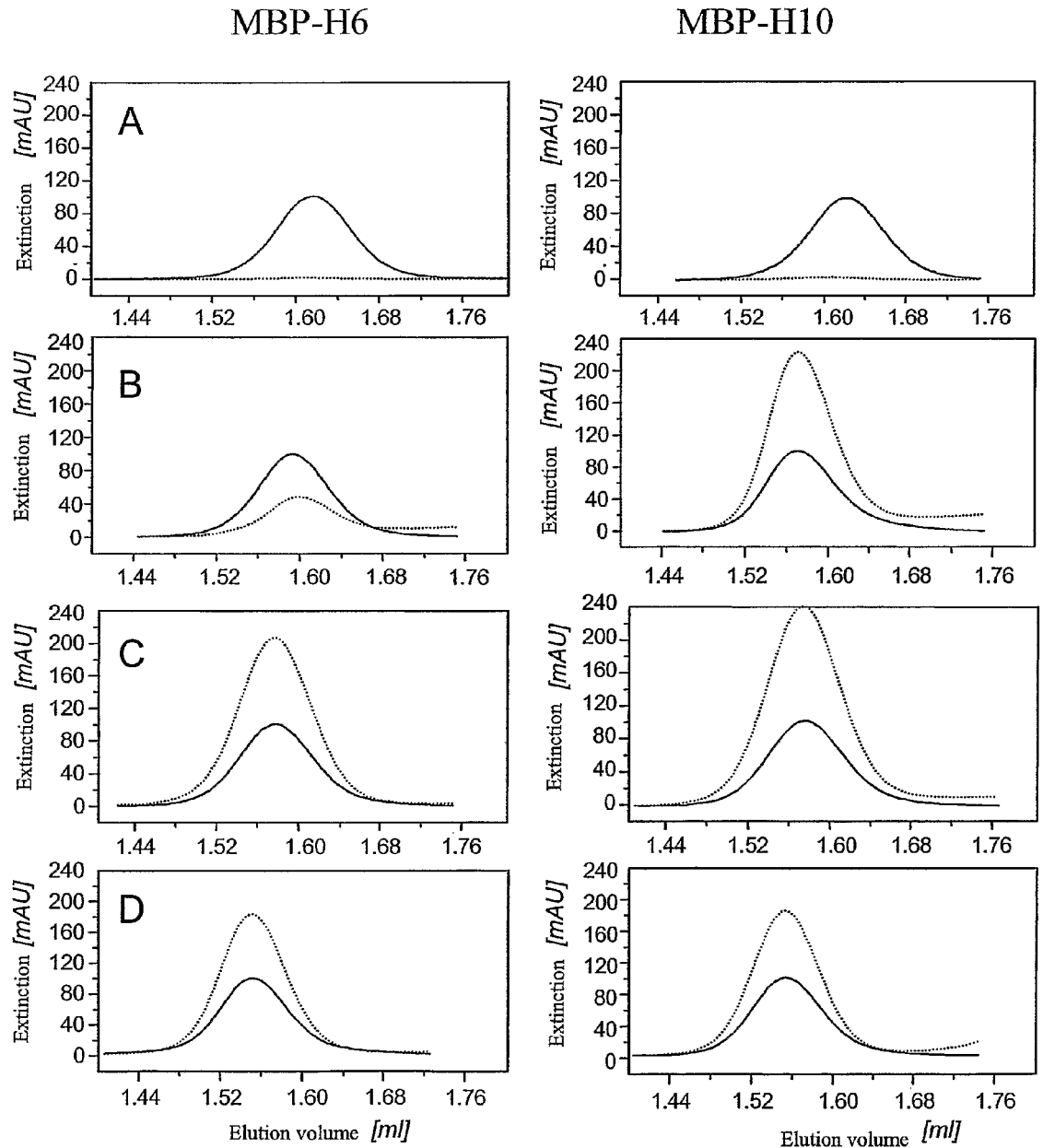

FIG. 21 shows the examination of the non-covalent fluorescent labeling of MBP-H6 (left side) and MBP-H10 (right side) with different MCH by means of analytical gel filtration (absorption at 280 nm (protein-), and at 490 nm (fluorescein . . . )).

(A) mono-NTA; (B) bis-NTA; (C) tris-NTA; (D) tetrakis-NTA (fluorescein-conjugates).

Figure 22:
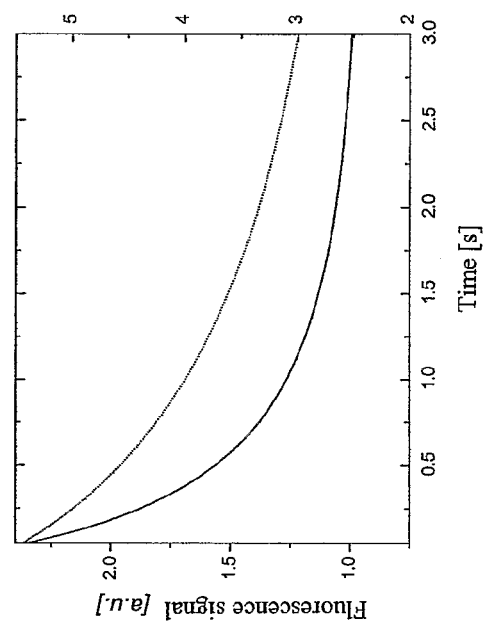

FIG. 22 shows the examination of the association kinetics by means of fluorescence quenching. Comparison of the binding curves for mono-NTA with H10-fluorescein (-), and H6-fluorescein ( . . . ).

Figure 23:
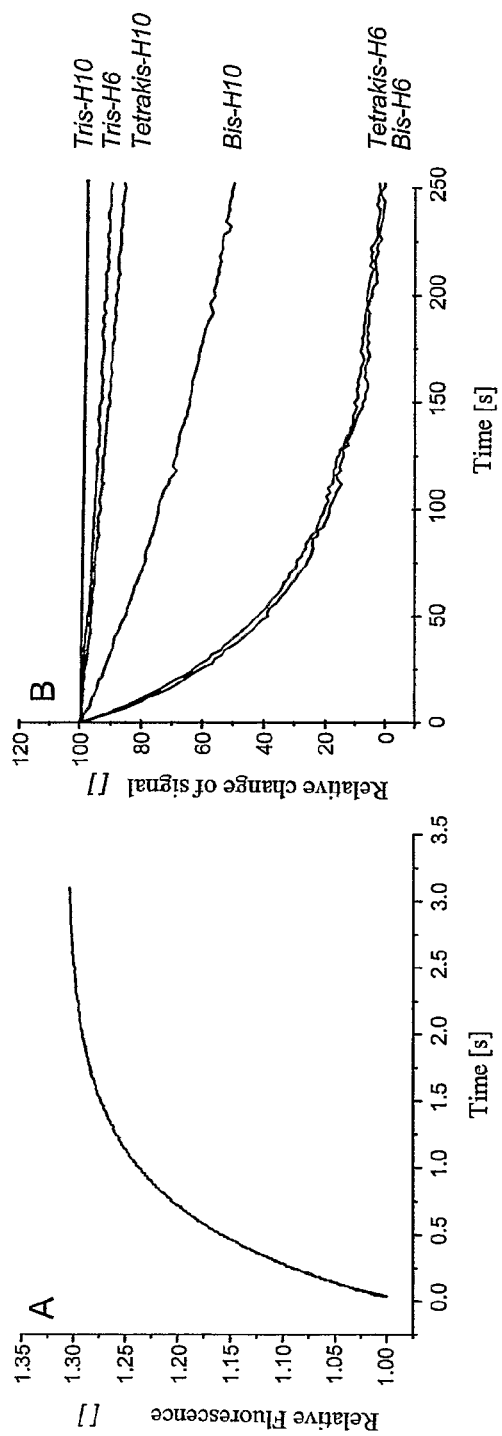

FIG. 23 shows the examination of the dissociation kinetics.

(A) change of fluorescence at 10-fold dilution of 5 mM mono-NTA-H10-fluorescein complex.

(B) the comparison of the dissociation kinetics for different MCH with H10-fluorescein, and H6-fluorescein normalized to the equilibrium-amplitude.

Figure 24:
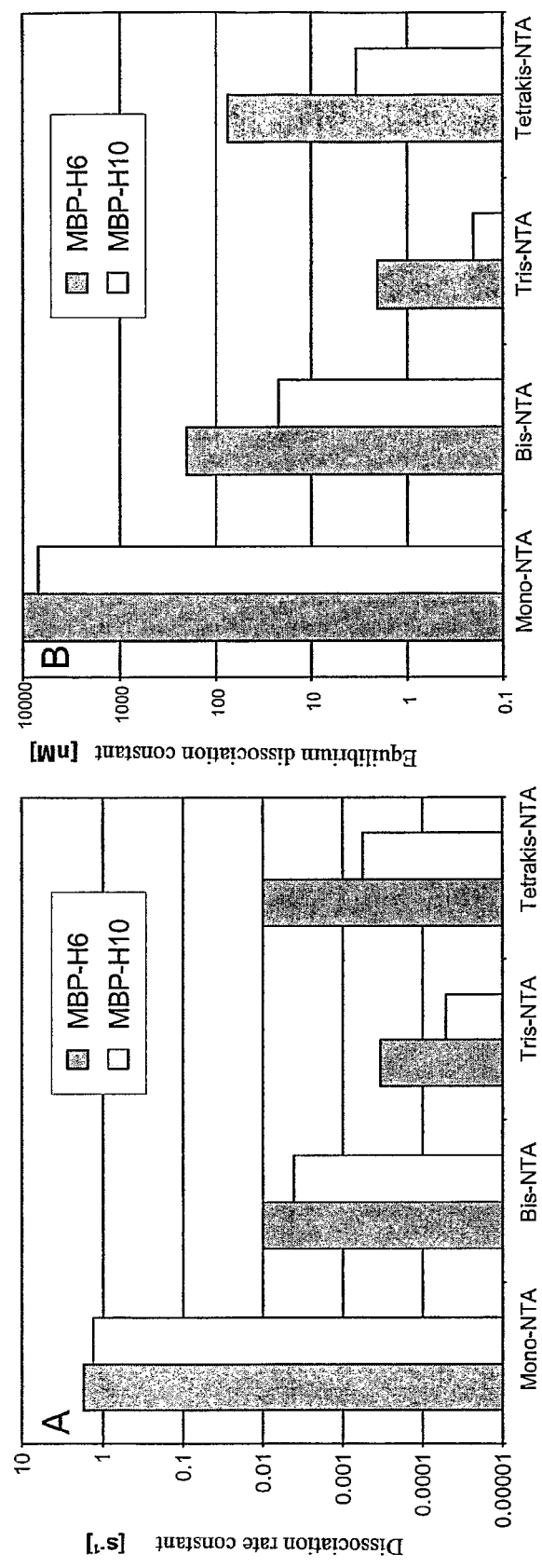

FIG. 24 shows the comparison of the complex formation constants for mono-NTA and MCH.

(A) dissociation rate constants, (B) equilibrium dissociation constants.

Figure 25:
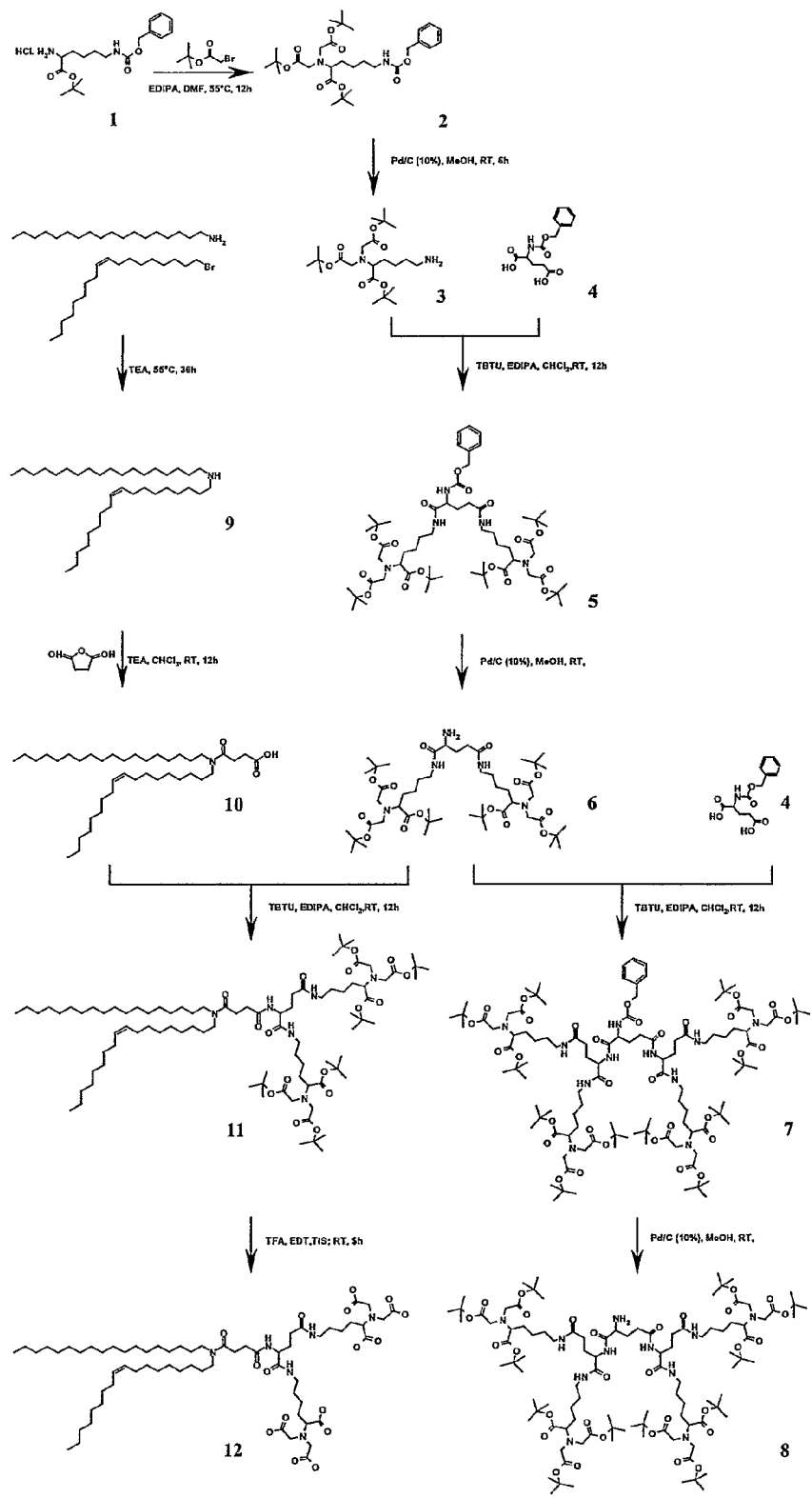

FIG. 25 shows the scheme for synthesis for the provision of bis-NTA-OtBu (6), tetrakis-NTA-OtBu (8) and a bis-NTA-lipid (12).

Figure 26:
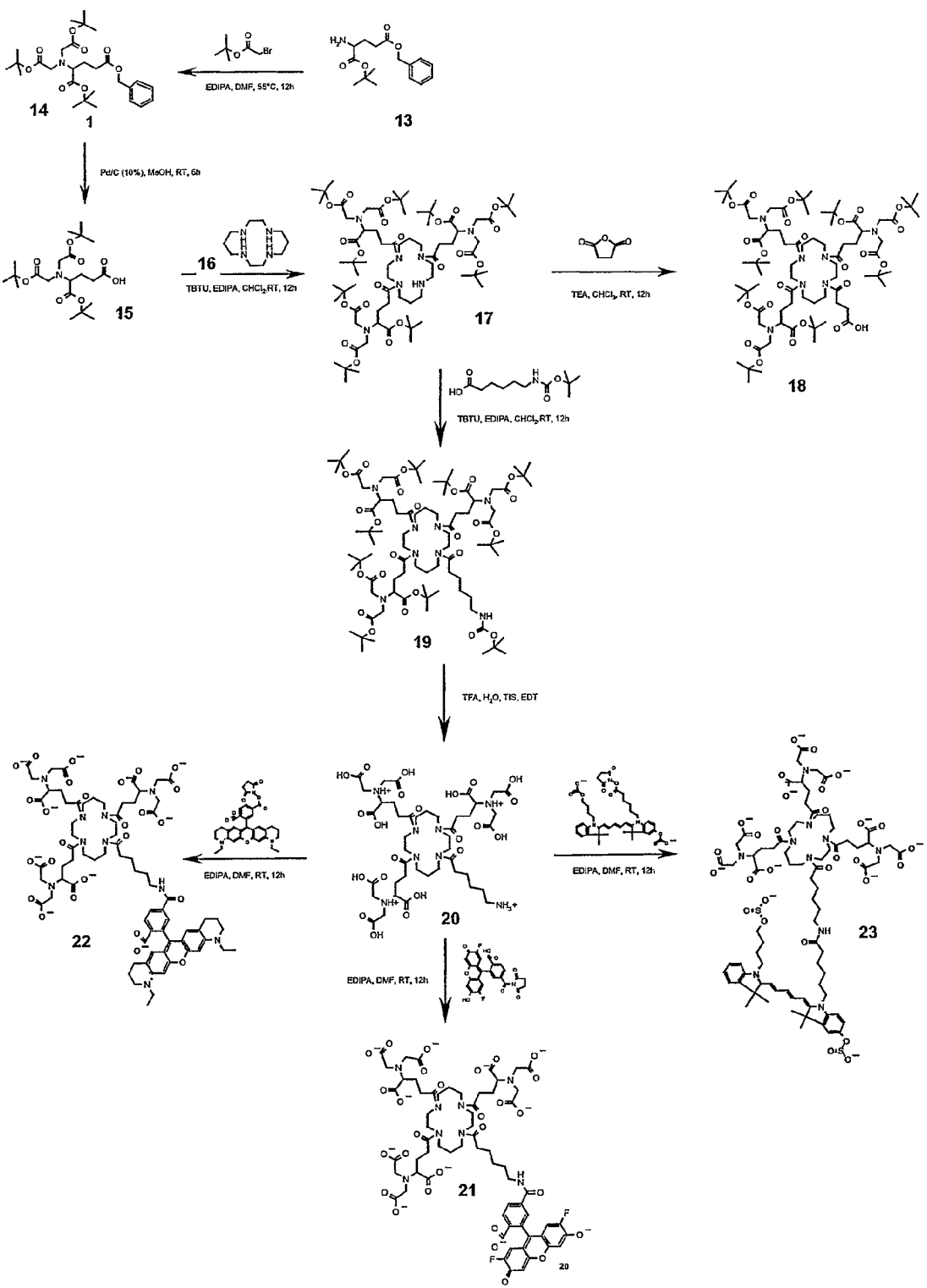

FIG. 26 shows the scheme for synthesis for the provision of tris-NTA-OtBu (17 and 18) and derivatives with three different fluorophores: Oregon Green 488 (21), ATTO 565 (22), FEW-S0387 (23).

EXAMPLE 1

Binding of MCH to Surfaces

For the immobilization of histidin-tagged proteins onto surfaces, the chelators were covalently attached onto glass and gold surfaces. For this, different strategies were used. First, gold surfaces were protected by means of a monolayer of α,ω-diamino-poly(ethylene glycol) (DAPEG, 2000 g/mol). This took place following a protocol against unspecific protein binding that was described by Piehler et al. 2000 (Piehler J, Brecht A, Valiokas R, Liedberg B, Gauglitz G. 2000. A high-density poly(ethylene glycol) polymer brush for immobilization on glass-type surfaces. *Biosensors & Bioelectronics* 15(9-10):473-481.)

Figure 1:
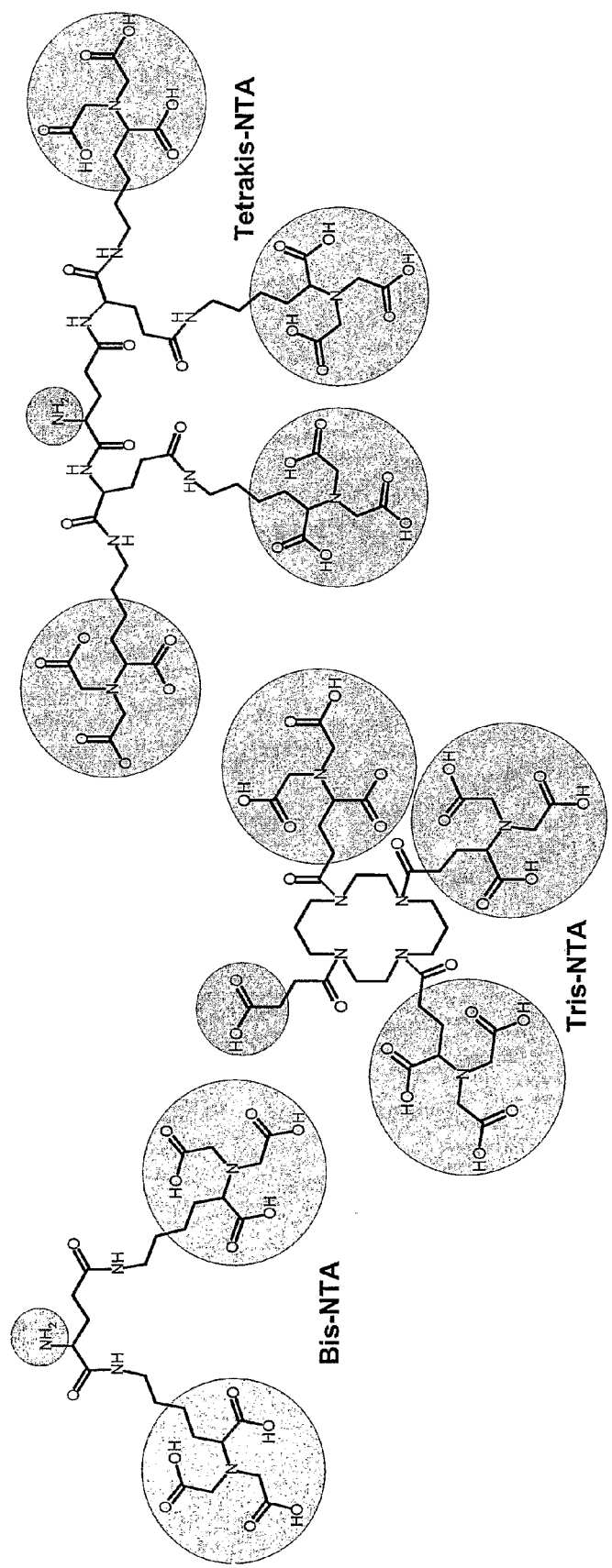
FIG. 1 shows the structural formulas of the multivalent chelators (MCH) and their principal composition. The NTA-groups are each hatched in light grey, and the coupling groups in dark grey.
Figure 2:
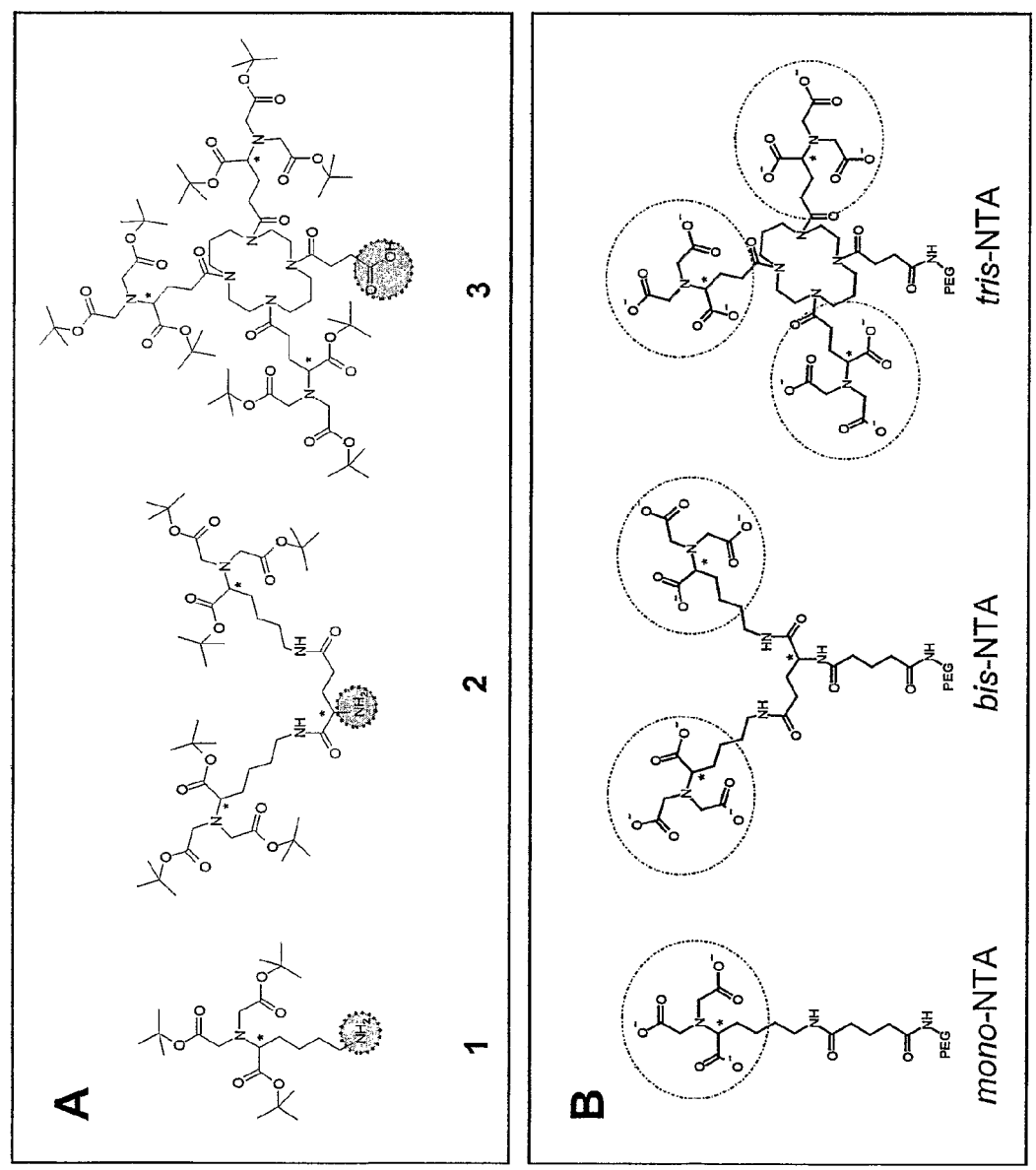
FIG. 2 shows the composition of the multivalent chelators.

The chemical attachment of the chelator to these surfaces is schematically depicted in FIG. 6. Carboxyl-functionalized chelator heads (cf. FIG. 2A) were directly coupled to the free amino groups of DAPEG (FIG. 6, Path III), whereby the surface concentration was varied by the duration of coupling. For the coupling of amino-functionalized chelators, the surface was first re-functionalized by means of glutaric acid anhydride (FIG. 6, Path I). The surface concentration of the carboxyl group was varied by the simultaneous addition of acetic acid anhydride (FIG. 6, Path II). The MCH were coupled to the so generated carboxyl groups. Subsequently, the protective group was removed by trifluoro acetic acid.

EXAMPLES 2-5

Immobilization of Proteins by MCH

EXAMPLE 2

Specific Immobilization and Functionality

The interaction of histidine-tagged proteins with the surfaces as produced in example 1 was characterized in detail by means of reflectometric interference spectroscopy (RIfS). Using this method, the binding of proteins to surfaces can be quantified in real time, as described in Piehler and Schreiber 2001 (Piehler J, Schreiber G. 2001. Fast transient cytokine-receptor interactions monitored in real time by reflectometric interference spectroscopy. *Anal. Biochem.* 289(2):173-186.)

The immobilization of the extracellular domain of ifnar2 with a C-terminal deca-histidine-tag (ifnar2-H10) to a tris-NTA modified surface (FIG. 7A) is shown in FIG. 7B. Whereas no binding was detectable before loading of the chelator coupled to the surface with Ni(II)-ions, thereafter an overall binding of about 1.5 ng/mm$^2$ protein was observed that also maintained stably immobilized during rinsing. Nevertheless, this protein could be removed quantitatively with 200 mM imidazole as competitor.

The functionality of the immobilized protein was examined through the binding of the ligand interferon α2 (IFNα2) (FIG. 8). Thereby, it could be found that more than 90% of the immobilized ifnar2-H10 were active and showed a specific reversible interaction with the ligand.

EXAMPLE 3

Self-Assembled Mono Layers (SAM) with MCHs

On gold surfaces, the technique of the self-assembled mono layers (SAM) was used (Sigal G B, Bamdad C, Barberis A, Strominger J, Whitesides G M. 1996. A self-assembled mono layer for the binding and study of histidine-tagged proteins by surface plasmon resonance. *Anal Chem* 68:490-7.).

For this, alkylthioles with bis-NTA head group were synthesized (FIG. 9A). In order to minimize unspecific protein interaction with the functionalized surfaces, an oligo (ethylene glycol) residue was introduced between the head group and alkyl group. This bis-NTA-thiol was mixed with a matrix thiol without MCH-head group (FIG. 9A) in order to generate SAMs with different surface concentrations of MCHs. A specific reversible immobilization of ifnar2-H6 as well as a specific binding of the ligand IFNα2 to the immobilized protein could be detected (FIG. 9B).

EXAMPLE 4

Stability of the Attachment Through MCH

The relative low stability of binding of mono-NTA at surfaces can be partially compensated by high surface concentrations of the chelator. In contrast to monovalent chelators MCHs allow for a stable binding of histidine-tagged proteins to surfaces also at low surface concentrations, which offers a series of advantages for the use. FIG. 10A primarily shows the binding of MBP-H10 to mono-NTA-functionalized surfaces.

After initially complete loading of the surface with protein (MBP-H10) a marked dissociation was observed: after 400 s more than 50% of the initially bound protein is dissociated from the surface. The observed dissociation kinetic can be explained by re-binding and cooperative effects at the surface which are typical for the binding through mono-NTA.

Compared to this, in case of the MCH a very stable binding and no significant dissociation in the same period of time could be observed (FIG. 10B). Since for the MCH no dissociation could be observed the binding stabilities were reduced by means of imidazole.

In FIG. 11A the dissociation of MBP-H10 of mono-NTA surfaces at different concentrations of imidazole is shown. The equilibrium loading $R_{eq}$ was determined by fitting of a binding model.

The dependency of $R_{eq}$ from the imidazole concentration for mono-, bis-, and tris-NTA is comparatively shown in FIG. 11B. A marked shift towards higher imidazole concentrations shows the increase of the binding stability as a function of the multivalence. In addition, steeper transitions are observed suggesting a transition to a molecular co-operativity in contrast to a surface-co-operativity of the mono-NTA.

Figure 12:
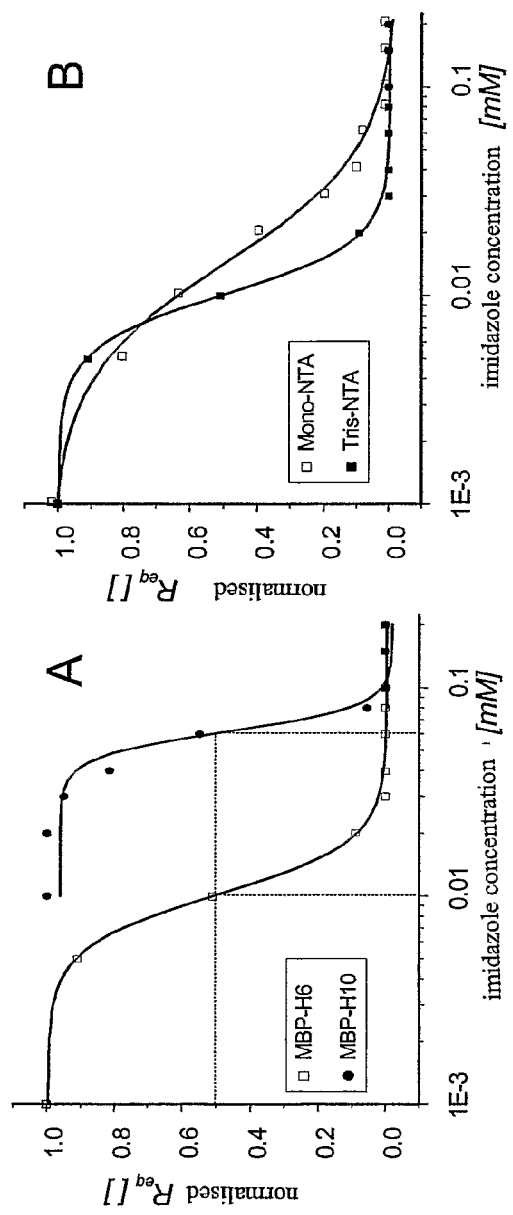

Using the same method in addition the stability of the binding through different histidine-tags was examined. For this, the maltose binding protein with a C-terminal hexa- (MBP-H6) and deca-histidine-tag (MBP-H10) was used. FIG. 12A shows a comparison of the imidazole-induced dissociation for these proteins of tris-NTA modified surfaces. The differences in the binding stability are so prominent that a quantitative distinction at 30 mM imidazole is possible. A markedly steeper transition compared with the interaction between mono-NTA and MBP-H10 again points to a molecular interaction (FIG. 12B).

EXAMPLE 5

Unspecific Binding

Unspecific binding of proteins with chelators—either electrostatically or via coordinated metal ions—is a central problem in the use of chelators for the immobilization of proteins, since a stable immobilization through mono-NTA requires a large excess of NTA-groups. This effect is demonstrated in FIG. 13A.

The ligand IFNβ to a high extent binds unspecifically to the surface being highly functionalized with mono-NTA, such that no reasonable binding kinetic can be determined. With tris-NTA, already a markedly lower unspecific binding can be recognized due to the low chelator concentration (FIG. 13B). By blocking of the binding sites with an indifferent protein (MBP-H10) the unspecific binding can be completely eliminated, and so to measure an undistorted binding kinetic. Since the coordinative sites at the surface can be quantitatively blocked, in this manner also specific interactions with histidine-tagged proteins can be examined.

An additional advantage of the high stability of the binding of the MCHs is found in the possibility, to efficiently block the binding of histidine-tagged proteins with the chelator-modified surface by the addition of metal ion-loaded MCH in solution. Thereby specific interaction with histidine-tagged proteins can be examined without that they bind to superfluous chelators at the surface. This is demonstrated in FIG. 14. With a low excess of tris-NTA in solution the binding of ifnar1-H10 to a tris-NTA-modified surface can be nearly completely suppressed (FIG. 14A).

Based on this principle, a binding assay was performed. For this, first ifnar2-H10 was immobilized on a tris-NTA-modified surface. After blocking of the excess of chelator with MBP-H10 the binding sites of the ifnar2 were saturated with IFNβ. The subsequent binding assay with ifnar1-H10 that was provided with tris-NTA-fluorescein (see below, example 8), is shown in FIG. 14B. Exclusively specific interaction was detected, while for the (inactive) mutant W129A in the binding site of IFNβ no binding was observed.

EXAMPLE 6

Conjugates with Lipids

For an attachment of proteins to lipid membranes, a lipid-analogue conjugate of bis-NTA was synthesized that is shown in FIG. 15A.

This lipid was incorporated into unilaminar vesicles of stearoyl-oleoyl-phosphatidylcholine that spontaneously form a fluid solid-supported lipid-double layer on glass surfaces (FIG. 15B). ifnar2-H10 could be specifically anchored at these membranes, whereby the binding activity was completely preserved (FIG. 15B). The lateral diffusion of the membrane-anchored ifnar2-H10 was analyzed through fluorescence-bleaching (fluorescence recovery after photobleaching, FRAP) (FIG. 16). Thereby, a diffusion constant of 1 μm²/s was determined.

EXAMPLES 7 AND 8

Conjugates with Fluorophores

EXAMPLE 7

Different Fluorophores and Spectroscopic Properties

For a non-covalent fluorescence labeling of histidine-tagged proteins in solution conjugates of tris-NTA with three different fluorophores were synthesized: Oregon Green 488, ATTO 565, FEW-S0387 (FIG. 17).

After loading with Ni(II)-ions ifnar2-H10 was added to these conjugates and the excess conjugate was separated through gel filtration.

A stable labeling of ifnar2-H10 was observed for all conjugates: in a second gel filtration run no free dye was detectable (FIG. 18A). Upon addition of the ligand, in addition a shift towards higher wavelengths was observed (FIG. 18A), and by this it was confirmed that the function of the protein was preserved by this position-specific labeling. This labeling was completely reversible: the MCH-fluorophore-conjugate could be completely separated through the addition of imidazole.

The different states of the MCH-fluorophore-conjugate could be followed by fluorescence quantum yield. (FIG. 18B). After loading of the chelator-groups with Ni(II)-ions a marked reduction of the fluorescence to about 50% was observed, and after binding to the protein to about 40%. This effect could also be observed at the other fluorescent dyes, and was even more pronounced at the fluorescent dye ATTO 565 (FIG. 19).

EXAMPLE 8

Binding Stability in Solution

For the examination of the binding stability in solution, conjugates of mono-, bis-, tris-, and tetrakis-NTA with fluorescein were synthesized, and loaded with Ni(II)-ions (FIG. 20). The interactions of these conjugates with hexa- and deca-histidine-tagged proteins were thermodynamically and kinetically characterized by means of analytical gel filtration, isothermic titration calorimetry, and fluorescence spectroscopy.

A) Analytical Gel Filtration

For the examinations by means of analytical gel filtration, MBP-H6 and MBP-H10 were provided with a stoichiometric excess of conjugate and these mixtures were loaded on the gel filtration-column, and the extinction was simultaneously monitored at the outlet of the column at 280 nm (protein) and 490 nm (fluorescein). Using the ratio of these signals, the level of labeling and thus the binding stability could be estimated. The chromatograms are summarized in FIG. 21. For mono-NTA (FIG. 21A), for MBP-H6, and MBP-H10 nearly no bound conjugate could be detected. For bis-NTA (FIG. 21B) a markedly more stable binding of MBP-H10 compared to MBP-H6 could be detected. For tris- and tetrakis-NTA (FIGS. 21C and 21D) stoichiometric levels of labeling and small differences between MBP-H6 and MBP-H10 could be detected.

These results show that the stability of the interaction of tris- and tetrakis-NTA with hexa-, and deca-histidine-tags is so high that a stable and stoichiometric fluorescence labeling can be achieved. In addition, they impressively demonstrate the superiority of the MCHs compared to the traditional mono-NTA in view of the stability of the interaction with histidine-tagged proteins.

B) Fluorescence Spectroscopy

The kinetics of the interaction between MCH and histidine-tags was examined by fluorescence spectroscopy. For this, fluorescein-labeled oligohistidine-peptides were used. Upon binding of these peptides to the MCHs, a strong fluorescence-quenching was observed. The change of the fluorescence was monitored by means of stopped-flow technique in high demand interval (cf. FIG. 22). From these curves, association rate constants of $1,5$-$5 \cdot 10^5$ $M^{-1}s^{-1}$ were determined through curve fitting. Thereby, the rate constants for deca-histidine were markedly higher as for hexa-histidine.

The same fluorescence-quenching-effect was also used for the examination of the dissociation kinetics. For this, first a stoichiometric complex at high concentration was produced and either diluted with buffer (for Mono-NTA) or a 10-fold excess of MBP-H10 (for MCH). In FIG. 23A the fluorescence-signal is shown that was observed upon dilution of a mono-NTA H10-fluorescein complex. From this curve, a dissociation rate constant of $1,5$ $s^{-1}$ was calculated, proving the extremely low stability of the molecular Ni:mono-NTA-histidine-tag complexes.

The stability of the MCH-oligohistidine-complexes was markedly higher, such that a competitor was required in order to observe dissociation. The so-obtained dissociation curves are shown in FIG. 23B. From these curves markedly lower dissociation rate constants were obtained as for mono-NTA (FIG. 24A). The resulting equilibrium-dissociation constants are shown in FIG. 24B which impressively confirm the increase of the binding affinities of the MCHs by nearly 5 magnitudes (to <1 nM) compared to mono-NTA (ca. 10 μM).

EXAMPLE 9

Instructions for Synthesis

A) Synthesis of Lys-NTA-OtBu (3) (See Also FIG. 25)

Bromoacetic acid tert-Butylester (1.59 ml; 10.8 mmol) and DIPEA (2.30 ml; 13.5 mmol) were added to a solution of $N^\epsilon$-benzyloxycarbonyl-L-lysine tert-butyl ester (1) (1.00 g; 2.7 mmol) in DMF (25 ml). The reaction flask is rinsed with nitrogen and then stirred over night at 55° C. The volatile components are drawn off in vacuo at 60° C. The residue is re-dissolved in cyclohexane/ethyl acetate (3:1, 15 ml), drawn off and the precipitate is washed three times with the same solvent (3×10 ml). The filtrate was concentrated and purified over a silica column with cyclohexane/ethyl acetate (3:1) as elution phase. Yield: 1.3 g (2.3 mmol) $N^\alpha,N^\alpha$-Bis[(tert-butyloxy-carbonyl)methyl]-N-benzyloxycarbonyl-L-lysine tert-butylester (2), 85% o.t.th. TLC: Rf=0.5 in cyclohexane/ethyl acetate (3:1)

$^1$H NMR (250 MHz, CDCl3); δ:
1.44 (s, 18H, $((CH_3)_3COCOCH_2)_2N$—);
1.47 (s, 9H, $(CH_3)_3COCOCH$—);
1.49 (m, 4H, Z—$NHCH_2$—$CH_2$—$CH_2$—);
1.59 (m, 2H, Z—NH—$(CH_2)_3CH_2$—);
3.20 (m, 2H, Z—$NHCH_2$—);
3.31 (t, 1H, $((CH_3)_3COCOCH_2)_2NCH$—);
3.46 (dd, 4H, $((CH_3)_3COCOCH_2)_2N$—);
5.07 (s, 2H, $(C_6H_5)CH_2OCONH$—);
5.13 (t, 1H, $(C_6H_5)CH_2OCONH$—);
7.33 (m, 5H, $(C_6H_5)CH_2$—);
MS (MALDI, ESI, $C_{30}H_{48}N_2O_8$); MH$^+$ 565

A solution of 1.00 g (1.8 mmol) 2 in methanol (50 ml) is rinsed with nitrogen and then 20 mg 10% Pd/C are added. The reaction mixture is vigorously stirred under hydrogen-atmosphere for 6 hours at room temperature. Pd/C is removed by filtration through celite, and the volatile components are drawn off in vacuo at. Yield: 0.74 g (1.7 mmol) $N^\alpha,N^\alpha$-Bis[(tert-butyloxycarbonyl)methyl]-L-lysine tert-butylester (3), 94% of the theory. TLC: $R_f$=0.3 in chloroform/methanol (3:1).

$^1$H NMR (250 MHz, CDCl3); δ:
1.44 (s, 18H, $((CH_3)_3COCOCH_2)_2N$—);
1.47 (s, 9H, $(CH_3)_3COCOCH$—);
1.51 (m, 4H, $NH_2CH_2$—$CH_2$—$CH_2$—)
1.62 (m, 2H, Z—NH—$(CH_2)_3CH_2$—);
2.69 (t, 2H, Z—$NHCH_2$—);
3.31 (t, 1H, $((CH_3)_3COCOCH_2)_2NCH$—);
3.47 (dd, 4H, $((CH_3)_3COCOCH_2)_2N$—);
MS (MALDI, ESI, $C_{22}H_{42}N_2O_6$); MH$^+$ 431

B) Synthesis of Bis-NTA-OtBu (6) (See Also FIG. 25)

3 (1.00 g; 2.3 mmol) is dissolved in dry dichloromethane (40 ml), and the 4 (0.29 g; 1.0 mmol), TBTU (0.96 g; 2.9 mmol) and DIPEA (0.6 ml; 3.5 mmol) are added. The obtained slurry is rinsed with nitrogen and stirred over night at room temperature. The volatile components are then removed in vacuo, the residue is slurried with dichloromethane (100 ml), and washed 3× with MQ water (30 ml each). The organic phase is dried over anhydrous sodium sulfate and concentrated in vacuo. The oily residue is purified over a silica column with cyclohexane/ethyl acetate (3:1) as eluent. Yield: 0.99 g (0.9 mmol) Z-Bis-NTA-OtBu (5), 90% o. theory. TLC: $R_f$=0.3 in cyclohexane/ethyl acetate (3:1).

$^1$H NMR (250 MHz, CDCl3); δ:
1.43 (s, 36H, $((CH_3)_3COCOCH_2)_2N$—);
1.45 (s, 18H, $(CH_3)_3COCOCH$—);
1.47-1.65 (m, 12H, $(CH_3)_3COCOCH(CH_2)_3$—)
1.96-2.04 (m, 2H, Z—$NHCHCH_2CH_2$—);

2.22-2.30 (m, 2H, Z—NHCHCH$_2$—);
3.14-3.22 (m, 6H, and ((CH$_3$)$_3$COCOCH$_2$)$_2$NCH(CH$_2$)$_3$CH$_2$—);
3.46 (dd, 8H, ((CH$_3$)$_3$COCOCH$_2$)$_2$N—);
4.17 (m, 1H, Z—NHCH—);
5.03 (s, 2H, (C$_6$H$_5$)CH$_2$OCONH—);
6.40 (d, 1H, Z—NH)
6.53 (t, 1H Z—NHCHCONH—)
6.99 (t, 1H Z—NHCH(CH$_2$)$_2$CONH—)
7.28 (m, 5H, (C$_6$H$_5$)CH$_2$—);
MS (MALDI, ESI, C$_{57}$H$_{95}$N$_5$O$_{16}$); MH$^+$ 1107

The Z-protective group of 5 (1.00 g; 0.90 mmol) is hydrogenolytically removed a described above for 2. Yield: 0.83 g (0.85 mmol) Bis-NTA-OtBu (6), 94% of the th. TLC: R$_f$=0.3 in chloroform/methanol (5:2).

$^1$H NMR (250 MHz, CDCl3); δ:
1.43 (s, 36H, ((CH$_3$)$_3$COCOCH$_2$)$_2$N—);
1.45 (s, 18H, (CH$_3$)$_3$COCOCH—);
1.47-1.65 (m, 12H, (CH$_3$)$_3$COCOCH(CH$_2$)$_3$—)
2.0-2.1 (m, 2H, Z—NHCHCH$_2$—);
2.37-2.44 (m, 2H, Z—NHCHCH$_2$CH$_2$—);
3.2-3.3 (m, 6H, and ((CH$_3$)$_3$COCOCH$_2$)$_2$NCH(CH$_2$)$_3$CH$_2$—);
3.36-3.50 (dd, 8H, ((CH$_3$)$_3$COCOCH$_2$)$_2$N—);
3.56 (t, 1H, Z—NHCH—);
5.03 (s, 2H, (C$_6$H$_5$)CH$_2$OCONH—);
6.88 (t, 1H Z—NHCH(CH$_2$)$_2$CONH—)
7.68 (t, 1H Z—NHCHCONH—)
MS (MALDI, ESI, C$_{49}$H$_{89}$N$_5$O$_{14}$); MH$^+$ 973

C) Synthesis of Tetrakis-NTA-OtBu (8) (See Also FIG. 25)

6 (1.00 g; 1.03 mmol) is dissolved in dry dichloromethane (30 ml), and then 4 (130 mg; 0.46 mmol), TBTU (1.40 mmol; 450 mg), and DIPEA (0.44 ml; 2.6 mmol) are added. The obtained reaction mixture is rinsed with nitrogen and stirred over night at room temperature. The volatile components are then removed in vacuo, the residue is slurried with dichloromethane (100 ml) and washed 3× with MQ water (30 ml each). The organic phase is dried over anhydrous sodium sulfate and concentrated in vacuo. The oily residue is purified over a silica column with ethyl acetate as eluent. Yield: 0.70 g (0.32 mmol) Z-tetrakis-NTA-OtBu (7), 70% o. th. TLC: R$_f$=0.3 in ethyl acetate.
MS (MALDI, ESI, C$_{111}$H$_{189}$N$_{11}$O$_{32}$); MH$^+$ 2189

The Z-protective group of 7 (1.00 g; 0.46 mmol) is hydrogenolytically removed a described above for 2. Yield: 0.86 g (0.42 mmol), 91%. Tetrakis-NTA-OtBu (8), 91% o.th. TLC: R$_f$=0.3 in chloroform/methanol (5:3).
MS (MALDI, ESI, C$_{103}$H$_{183}$N$_{11}$O$_{30}$); MH$^+$ 2055

D) Synthesis Von Tris-NTA-OtBu (17 or 18) (See Also FIG. 26)

Bromoacetic acid tert-butylester (5.9 ml; 40 mmol), and DIPEA (8.6 ml; 50 mmol) are added to a solution of H-Glu(OtBu)-OBzl 13 (3.3 g; 10 mmol) in DMF (75 ml). The reaction flask is rinsed with nitrogen and then stirred over night at 55° C. The volatile components are drawn off in vacuo at 60° C. The residue is slurried in ethyl acetate (20 ml), filtered off and washed three times with cyclohexane: ethyl acetate (3:1, 3×40 ml). The filtrate was concentrated in vacuo and purified over a silica column with cyclohexane: ethyl acetate (3:1) as eluent. Yield: 4.6 g (8.8 mmol) Bzl-Glu-NTA (14), 88% d. Th. TLC: R$_f$=0.6 in cyclohexane: ethyl acetate (3:1)
MS (MALDI, ESI, C$_{28}$H$_{43}$NO$_8$); MH$^+$ 522

The Bzl-protective group of 14 (1.00 g; 1.9 mmol) is hydrogenolytically removed a described above for the removal of the Z-protective group of 2. Yield: 0.76 g (1.76 mmol) Glu-NTA (15), 92% d. Th. TLC: R$_f$=0.4 in chloroform/methanol (3:2)
MS (MALDI, ESI, C$_{21}$H$_{37}$NO$_8$); MH$^+$ 431

15 (431 mg; 1.0 mmol) is dissolved in dry dichloromethane (30 ml), and then 16 (67 mg; 0.33 mmol), TBTU (417 mg; 1.3 mmol), and DIPEA (0.3 ml; 1.75 mmol) are added. The obtained reaction mixture is rinsed with nitrogen and stirred over night at room temperature. The volatile components are then drawn off in vacuo, the residue is slurried with dichloromethane (50 ml) and washed 3× with MQ water (15 ml each). The organic phase is dried over anhydrous sodium sulfate, and concentrated in vacuo. The oily residue is purified over a silica column with a gradient of 100% ethyl acetate to 50% ethyl acetate in methanol in 5 volumes of the column.

Yield: 0.37 g (0.26 mmol) Tris-NTA-OtBu (17), 79% o.th. TLC: R$_f$=0.5 in ethyl acetate/methanol (3:1)
MS (MALDI, ESI, C$_{73}$H$_{129}$N$_7$O$_{21}$); MH$^+$ 1441

17 (1.44 g; 1.0 mmol) is dissolved in dry chloroform (30 ml), and succinic acid anhydride (300 mg; 3.0 mmol) and TEA (0.7 ml; 5.0 mmol) are added. The obtained reaction mixture is rinsed with nitrogen and stirred over night at room temperature. The volatile components are then drawn off in vacuo, the residue is slurried with dichloromethane (120 ml) and washed 3× with MQ water (40 ml each). The organic phase is dried over anhydrous sodium sulfate, and concentrated in vacuo. The oily residue is purified over a silica column with a gradient of 100% ethyl acetate to 50% ethyl acetate in methanol in 5 volumes of the column. Yield: 1,4 g (0.91 mmol) Tris-NTA-OtBu-COOH (18), 91% o.th. TLC: R$_f$=0.4 in ethyl acetate/methanol (3:1).
MS (MALDI, ESI, C$_{76}$H$_{133}$N$_7$O$_{24}$); MH$^+$ 1541

E) Synthesis of the Tris-NTA Fluorescence-Conjugates (See Also FIG. 26)

17 (1.44 g, 1.0 mmol,) is dissolved in dry dichloromethane (30 ml), and then BOC-☐-aminocaproic acid (230 mg; 1.0 mmol), TBTU (450 mg; 1.40 mmol), and DIPEA (0.33 ml; 1.9 mmol) are added. The reaction mixture is rinsed with nitrogen and stirred for 12 hours at room temperature. The volatile components are then drawn off in vacuo, the residue is slurried with dichloromethane (70 ml) and washed 3× with MQ water (25 ml each). The organic phase is dried over anhydrous sodium sulfate, and concentrated in vacuo. The oily residue is purified over a silica column with a gradient of 100% ethyl acetate to 10% ethyl acetate in methanol in 5 volumes of the column. TLC: Yield: 1.4 g (0.84 mmol) Tris-NTA-OtBu-aminocaproic acid-BOC (19), 84% o.th. R$_f$=0.3 in ethyl acetate
MS (MALDI, ESI, C$_{84}$H$_{148}$N$_8$O$_{24}$); MH$^+$ 1654

19 (500 mg; 0.3 mmol) is dissolved in dichloromethane with 10% TFA and 1% 1,2-ethandithiol, and stirred for 1 h. Then, the product is precipitated with ether. Yield 300 mg (0.3 mmol) Tris-NTA-aminocaproic acid (20), 95% o.th.
MS (MALDI, ESI, C$_{43}$H$_{68}$N$_8$O$_{22}$); MH$^+$ 1049

20 (10 mg; 0.05 mmol) is dissolved in 100 μl DMF and provided with a stoichiometric amount of an NHS-active ester of the corresponding fluorescent dye. After 12 hours the product is first purified by through preparative thin-layer chromatography, and then by anionic exchange-chromatography.

OG 488-Tris-NTA (21)
MS (MALDI, ESI, C$_{64}$H$_{65}$F$_2$N$_8$O$_{28}$); MH$^+$ 1432
ATTO 565-Tris-NTA (22)
MS (MALDI, ESI, C$_{74}$H$_{87}$N$_{10}$O$_{26}$); MH$^+$ 1532
FEW-S0387 tris-NTA (23)
MS (MALDI, ESI, C$_{78}$H$_{101}$N$_{10}$O$_{29}$S$_2$); MH$^+$ 1706

F) Synthesis of the Bis-NTA Lipid-Conjugates (12) (See Also FIG. 25)

Octadecylamine (2.7 g; 10 mmol), 1-Bromo-cis-9-octadecene (3.3 g; 10 mmol) and TEA (7 ml, 50 mmol) are mixed. The reaction flask is rinsed with nitrogen and stirred at 55 C for 2 days. The crude product is dissolved in chloroform (200 ml) and 3× with water washed (50 ml each). The organic phase is concentrated and purified over a silica column with a gradient of 100% chloroform auf 60% chloroform in methanol over 5 volumes of the column. Yield: 2.1 g (4.05 mmol) Steroyl-oleoyl-amine, SOA (9), 40% o.th.

$^1$H NMR (250 MHz, CDCl3); δ:

0.89 (t, 6H, $CH_3(CH_2)_{15}CH_2CH_2NHCH_2CH_2(CH_2)_5CH_2CHCHCH_2(CH_2)_6CH_3$);

1.27 (s, 52H, $CH_3(CH_2)_{15}CH_2CH_2NHCH_2CH_2(CH_2)_5CH_2CHCHCH_2(CH_2)_6CH_3$)

1.91 (q, 4, $CH_3(CH_2)_{15}CH_2CH_2NHCH_2CH_2(CH_2)_5CH_2CHCHCH_2(CH_2)_6CH_3$)

2.01 (q, 4, $CH_3(CH_2)_{15}CH_2CH_2NHCH_2CH_2(CH_2)_5CH_2CHCHCH_2(CH_2)_6CH_3$)

2.94 (t, 4, $CH_3(CH_2)_{15}CH_2CH_2NHCH_2CH_2(CH_2)_5CH_2CHCHCH_2(CH_2)_6CH_3$)

5.36 (q, 2, $CH_3(CH_2)_{15}CH_2CH_2NHCH_2CH_2(CH_2)_5CH_2CHCHCH_2(CH_2)_6CH_3$)

MS (MALDI, ESI, $C_{36}H_{73}N$); MH$^+$ 521

Succinic acid anhydride (0.60 g; 6 mmol) and TEA (2.5 ml; 18 mmol) are added to a solution of 9 (1.04 g; 2 mmol) in chloroform (50 ml). The reaction flask is rinsed with nitrogen and stirred over night at room temperature. The crude product is washed with MQ-water (4×40 ml). The organic phase is dried, concentrated and precipitated with acetone. Yield: 1.18 g (1.9 mmol) SOA-COOH (10), 95% o.th.

$^1$H NMR (250 MHz, CDCl3); δ:

0.88 (t, 6H, $CH_3(CH_2)_{15}CH_2CH_2NHCH_2CH_2(CH_2)_5CH_2CHCHCH_2(CH_2)_6CH_3$);

1.27 (s, 52H, $CH_3(CH_2)_{15}CH_2CH_2NHCH_2CH_2(CH_2)_5CH_2CHCHCH_2(CH_2)_6CH_3$)

1.54 (q, 4H, $CH_3(CH_2)_{15}CH_2CH_2NHCH_2CH_2(CH_2)_5CH_2CHCHCH_2(CH_2)_6CH_3$)

2.00 (q, 4H, $CH_3(CH_2)_{15}CH_2CH_2NHCH_2CH_2(CH_2)_5CH_2CHCHCH_2(CH_2)_6CH_3$)

2.69 (t, 4H, $CH_3(CH_2)_{15}CH_2CH_2NHCH_2CH_2(CH_2)_5CH_2CHCHCH_2(CH_2)_6CH_3$)

3.22 (t, 2H, $OHCOCH_2CH_2CONH$—)

3.30 (t, 2H, $OHCOCH_2CH_2CONH$—)

5.34 (q, 2, $CH_3(CH_2)_{15}CH_2CH_2NHCH_2CH_2(CH_2)_5CH_2CHCHCH_2(CH_2)_6CH_3$)

MS (MALDI, ESI, $C_{40}H_{77}NO_3$); MH$^+$ 620

10 (530 mg; 0.85 mmol) was dissolved in dry dichloromethane (30 ml), and then 6 (834 mg; 0.86 mmol), TBTU (413 g, 1.29 mmol), and DIPEA (0.3 ml, 1.76 mmol) are added. The reaction solution is rinsed with nitrogen and stirred for 12 h at room temperature. The volatile components are then removed in vacuo, and the residue is taken up with dichloromethane (30 ml). After washing with MQ water (3×30 ml) the organic phase is dried over anhydrous sodium sulfate. The volatile components are then removed in vacuo, and the residue purified over a silica column with chloroform/ethyl acetate (3:2). Yield: 0.97 g (0.61 mmol) SOA-bis-NTA-OtBu (11), 71% o.th. TLC: R$_f$=0.6 in chloroform/ethyl acetate (3:2).

$^1$H NMR (250 MHz, CDCl3); δ:

0.87 (t, 6H, $CH_3(CH_2)_{15}CH_2CH_2NHCH_2CH_2(CH_2)_5CH_2CHCHCH_2(CH_2)_6CH_3$)

1.25 (s, 52H, $CH_3(CH_2)_{15}CH_2CH_2NHCH_2CH_2(CH_2)_5CH_2CHCHCH_2(CH_2)_6CH_3$)

1.45 (s, 36H, $((CH_3)_3COCOCH_2)_2N$—);

1.46 (s, 18H, $(CH_3)_3COCOCH$—);

1.47-3.5 (H)

4.37 (m, 1H, NHCH—)

5.34 (q, 2, $CH_3(CH_2)_{15}CH_2CH_2NHCH_2CH_2(CH_2)_5CH_2CHCHCH_2(CH_2)_6CH_3$)

6.58 (t, 1H, NH)

7.42 (t, 1H, NH)

7.61 (t, 1H, NH)

MS (MALDI, ESI, $C_{89}H_{164}N_6O_{16}$); MNa$^+$ 1592

11 (500 mg; 0.32 mmol) is dissolved in dichloromethane with 10% TFA and 1% 1,2-ethanedithiol, and stirred for 1 h. Then, the product is precipitated with ether. Yield: 370 mg (0.3 mmol) SOA-bis-NTA (12), 94% o.th.

$^1$H NMR (250 MHz, CDCl3); δ:

0.87 (t, 6H, $CH_3(CH_2)_{15}CH_2CH_2NHCH_2CH_2(CH_2)_5CH_2CHCHCH_2(CH_2)_6CH_3$)

1.25 (s, 52H, $CH_3(CH_2)_{15}CH_2CH_2NHCH_2CH_2(CH_2)_5CH_2CHCHCH_2(CH_2)_6CH_3$)

1.47-3.5 (H)

5.03 (m, 1H, NHCH—)

5.34 (q, 2, $CH_3(CH_2)_{15}CH_2CH_2NHCH_2CH_2(CH_2)_5CH_2CHCHCH_2(CH_2)_6CH_3$)

MS (MALDI, ESI, $C_{65}H_{111}N_6O_{16}$); MH$^+$ 1233

The invention claimed is:

1. A compound selected from

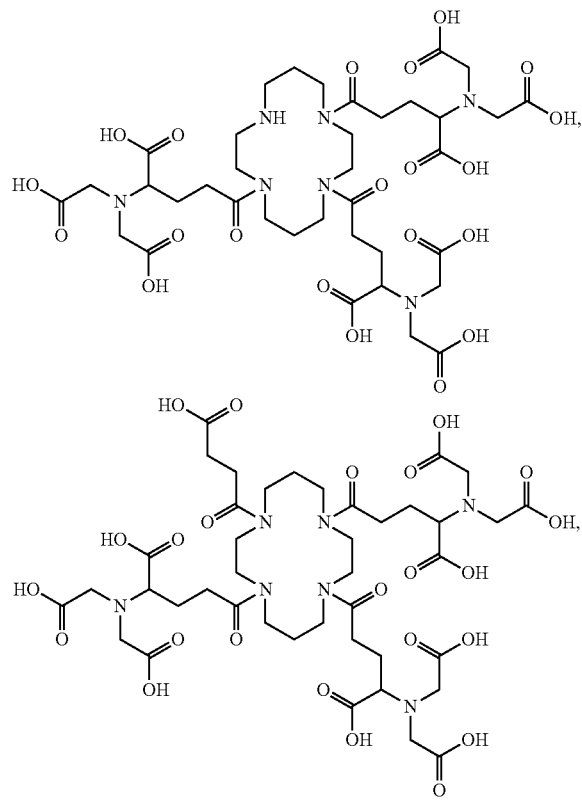

-continued

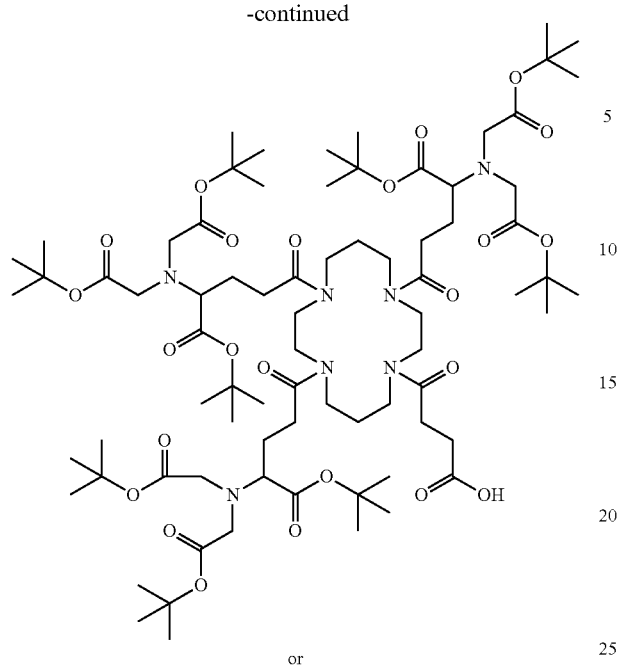

or

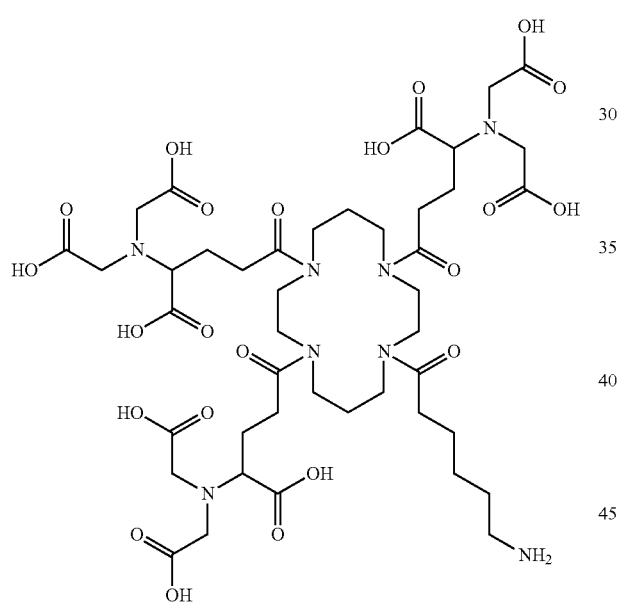

or an anhydride or salt thereof.

2. The compound according to claim 1, further comprising a probe or functional unit F, wherein the compound is bound to the probe or functional unit F; wherein the probe or functional unit F is selected from the group consisting of a fluorophore, fluorescence quencher, phosphorescent compound, luminescent compound, PEG, oligosaccharide, oligonucleotide, PNA, biotin, haptene, peptide, enzyme, crosslinking agent, oligoethyleneglycol, lipid, nanoparticle, electron density amplifier, metal cluster, and a quantum dot, or a combination thereof.

3. The compound according to claim 1, further comprising a probe or functional unit F, wherein the compound is bound to the probe or functional unit F; wherein the probe or functional unit F is selected from the group consisting of an absorbing compound, polymer, and protein, or a combination thereof.

4. A compound selected from

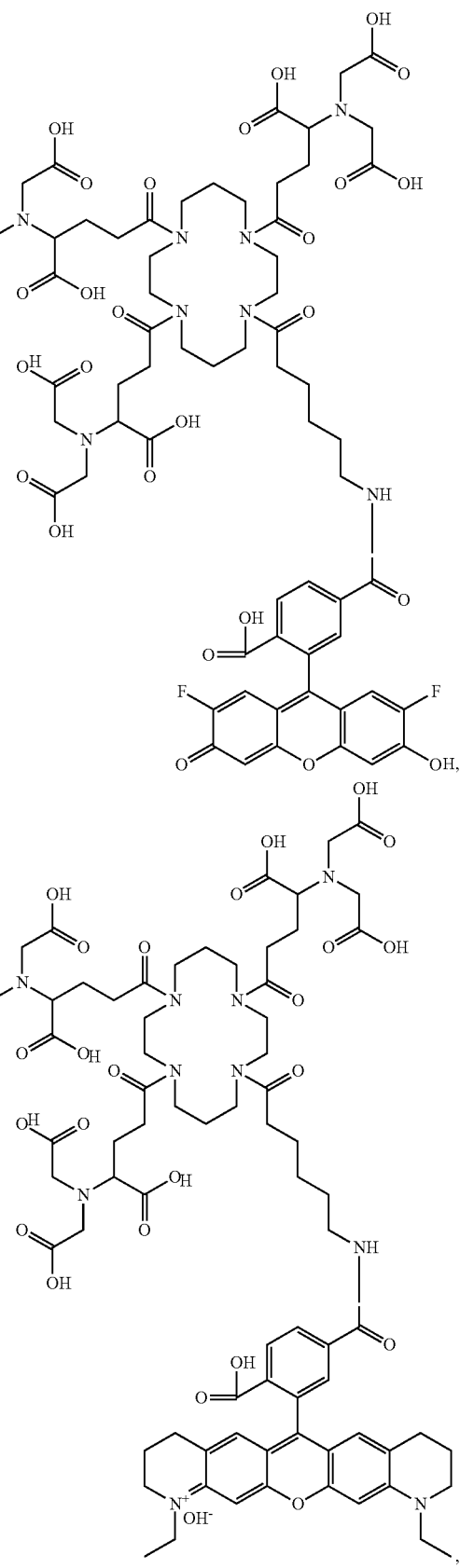

-continued

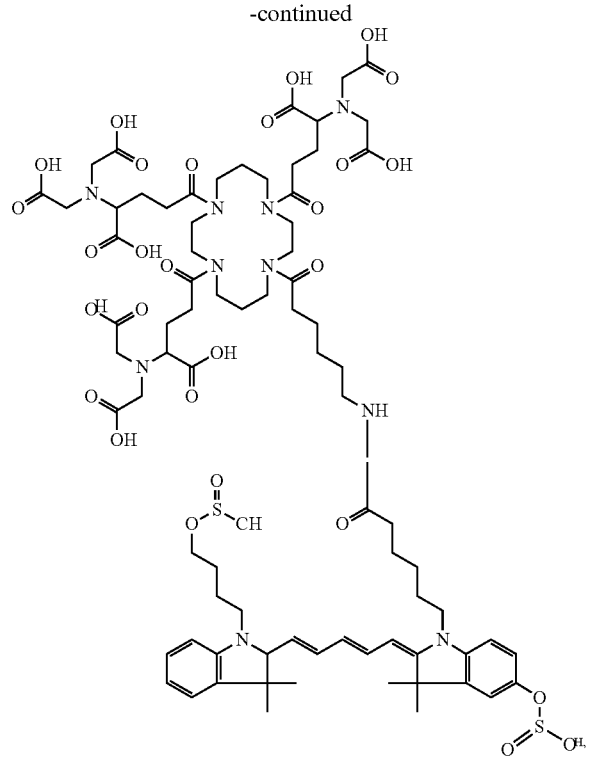

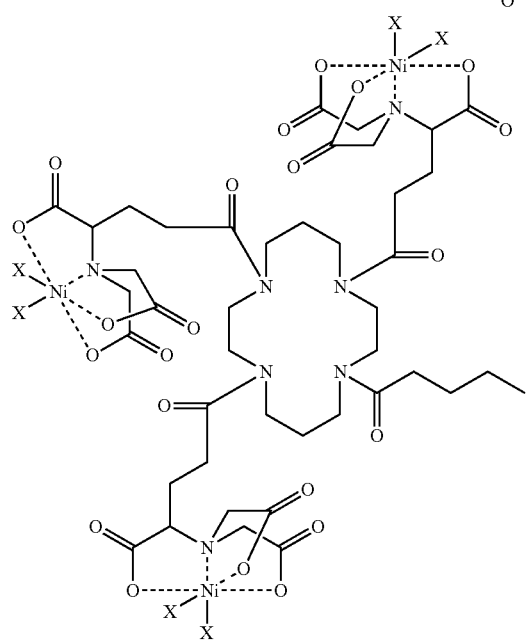

or

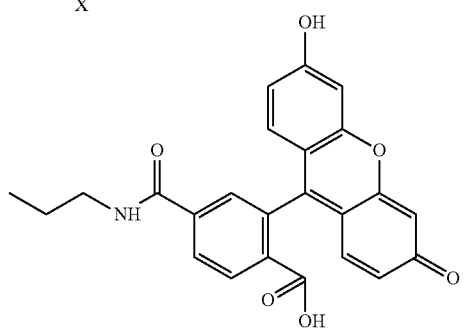

-continued

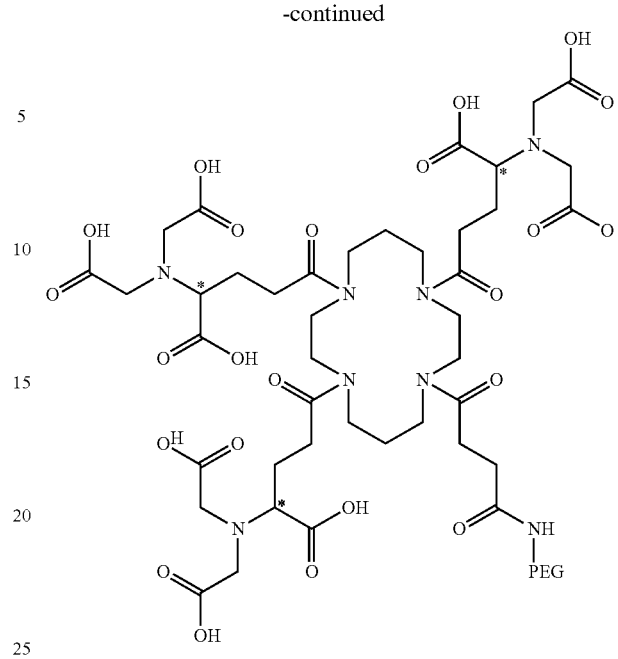

or a tautomer, anhydride or salt thereof.

5. A compound of formula (II)

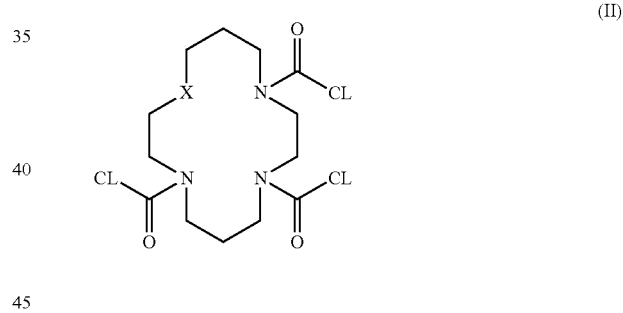

(II)

wherein

X is selected from the group consisting of NHR, wherein R is H, alkyl or aryl; $(CH_2)_n$—COOH, wherein n is an integer in a range from 0 to 2; SH; maleimide; acetamide; isothiocyanate and cyanate, CL is a chelator-group with a metal-coordinative center, selected from the group consisting of nitrilotriacetic acid (NTA), iminodiacetic acid (IDA), porphyrine systems, 1,2-diaminoethyldiacetic acid, diaminoethyl triacetic acid, hydroxy ethylimino diacetic acid, and a salt, or a combination thereof;

and wherein optionally a spacer group A is located between CL and the scaffold-structure, wherein the spacer group is selected from the group consisting of poly(ethylene glycol), oligo(ethylene glycol), peptides, $(CH_2)_z$ with z being from 1 to 8 and oligoproline;

or a tautomer, anhydride, acid or a salt thereof.

6. The compound according to claim 5, wherein the compound is

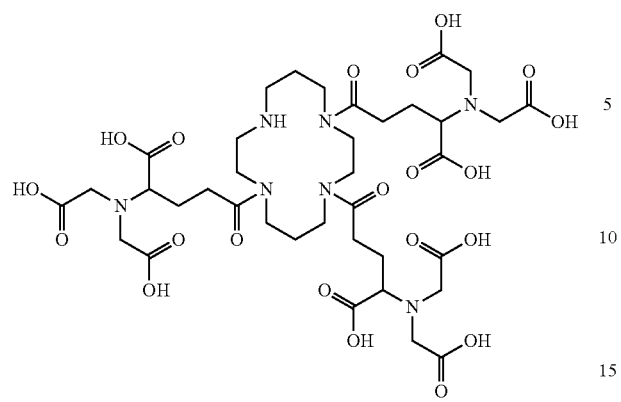

or a tautomer, anhydride or salt thereof.

7. The compound according to claim 5, wherein a probe or functional unit F is bound at X; wherein the probe or functional unit F is selected from the group consisting of a fluorophore, fluorescence quencher, phosphorescent compound, luminescent compound, PEG, oligosaccharide, oligonucleotide, PNA, biotin, haptene, peptide, enzyme, crosslinking agent, oligoethyleneglycol, lipid, nanoparticle, electron density amplifier, metal cluster, and a quantum dot, or a combination thereof.

8. The compound according to claim 5, wherein a probe or functional unit F is bound at X; wherein the probe or functional unit F is selected from the group consisting of an absorbing compound, polymer, and protein, or a combination thereof.

* * * * *